(12) United States Patent  
Kieu et al.

(10) Patent No.: US 8,792,156 B1  
(45) Date of Patent: Jul. 29, 2014

(54) LASER ILLUMINATION SYSTEMS AND METHODS FOR DUAL-EXCITATION WAVELENGTH NON-LINEAR OPTICAL MICROSCOPY AND MICRO-SPECTROSCOPY SYSTEMS

(75) Inventors: Khanh Kieu, Tuscon, AZ (US); Nasser Peyghambarian, Tuscon, AZ (US); Xiaoliang Sunney Xie, Lexington, MA (US); Christian W. Freudiger, Cambridge, MA (US); Dan Fu, Somerville, MA (US)

(73) Assignees: President and Fellows of Harvard College, Cambridge, MA (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 232 days.

(21) Appl. No.: 13/351,831

(22) Filed: Jan. 17, 2012

(51) Int. Cl.
*H01S 3/10* (2006.01)
*G01J 3/44* (2006.01)
*G02F 1/37* (2006.01)

(52) U.S. Cl.
USPC .............. 359/327; 359/326; 356/301; 372/25

(58) Field of Classification Search
USPC ............. 359/326–332; 372/25; 356/301, 337, 356/342
See application file for complete search history.

(56) References Cited

U.S. PATENT DOCUMENTS

| 5,530,582 | A | 6/1996 | Clark |
| 6,034,975 | A | 3/2000 | Harter et al. |
| 6,108,081 | A | 8/2000 | Holtom et al. |
| 6,809,814 | B2 | 10/2004 | Xie et al. |
| 6,885,683 | B1 | 4/2005 | Fermann et al. |
| 6,990,270 | B2 | 1/2006 | Nicholson |
| 7,167,300 | B2 | 1/2007 | Fermann et al. |
| 7,218,443 | B2 | 5/2007 | Tauser et al. |
| 7,414,729 | B2 | 8/2008 | Xie et al. |
| 7,616,304 | B2 * | 11/2009 | Gankkhanov et al. ........ 356/301 |
| 8,027,032 | B2 | 9/2011 | Xie et al. |
| 8,446,580 | B2 * | 5/2013 | Cerullo et al. ................. 356/301 |
| 2005/0238070 | A1 * | 10/2005 | Imeshev et al. .................. 372/21 |
| 2006/0146898 | A1 | 7/2006 | Tauser et al. |
| 2008/0037595 | A1 | 2/2008 | Gankkhanov et al. |
| 2010/0188496 | A1 | 7/2010 | Xie et al. |
| 2011/0280262 | A1 | 11/2011 | Fermann et al. |
| 2011/0280263 | A1 | 11/2011 | Kieu et al. |
| 2013/0064256 | A1 | 3/2013 | Xu et al. |

OTHER PUBLICATIONS

Kielpinski et al., "Mode-locked picosecond pulse generation from an octave-spanning supercontinuum" Optical Society of America, Nov. 9, 2009, vol. 17, No. 23, Optics Express, pp. 20833-20839.

(Continued)

*Primary Examiner* — Daniel Petkovsek
(74) *Attorney, Agent, or Firm* — Gesmer Updegrove LLP

(57) ABSTRACT

An illumination system is disclosed for providing dual-excitation wavelength illumination for non-linear optical microscopy and micro-spectroscopy. The illumination system includes a laser system, an optical splitting means, a frequency shifting system, and a picosecond amplifier system. The laser system includes a laser for providing a first train of pulses at a center optical frequency $\omega_1$. The optical splitting means divides the first train of pulses at the center optical frequency $\omega_1$ into two trains of pulses. The frequency shifting system shifts the optical frequency of one of the two trains of pulses to provide a frequency shifted train of pulses. The picosecond amplifier system amplifies the frequency shifted train of pulses to provide an amplified frequency-shifted train of pulses having a pulse duration of at least 0.5 picoseconds.

21 Claims, 19 Drawing Sheets

(56) References Cited

OTHER PUBLICATIONS

Pegoraro et al., "All-fiber CARS microscopy of live cells" Optics Express, Nov. 9, 2009, No. 23, pp. 20700-20706.
Gambetta et al., "Fiber-format stimulated-Raman-scattering microscopy from a single laser oscillator" Optics Letters, vol. 35, No. 2, Jan. 15, 2010, Optical Society of America, pp. 226-228.
Krauss et al., "Compact coherent anti-stokes Raman scattering microscope based on a picosecond two-color Er: fiber laser system" Optics Letters, vol. 34, No. 18, Sep. 15, 2009, pp. 2847-2849.
Wang et al., "Synchronized time-lens source for coherent Raman scattering microscopy" Optics Express, vol. 18 Nov. 8, 2010, vol. 18, No. 23, Optical Society of America, pp. 24019-24024.
Zhai et al., "Multimodal coherent anti-Stokes Raman spectroscopic imaging with a fiber optical parametric oscillator" Applied Physics Letters, 98, 2011, American Institute of Physics, pp. 191106-1-191106-3.
Kieu et al., "High-power picosecond fiber source for coherent Raman microscopy" Optics Letters, vol. 34, No. 13, Jul. 1, 2009, Optical Society of America, pp. 2051-2053.
Ganikhanov et al., "Broadly tunable dual-wavelength light source for coherent anti-Stokes Raman scattering microscopy" Optics Letters, vol. 31, No. 9, May 1, 2006, Optical Society of America, pp. 1292-1294.
Dykaar et al., "Sticky pulses: two-color cross-mode-locked femtosecond operation of a single Ti:sapphire laser" Optics Letters, vol. 18, No. 8, Apr. 15, 1993, Optical Society of America, pp. 634-636.
Potma et al., "High-sensitivity coherent anti-Stokes Raman scattering microscopy with two tightly synchronized picosecond lasers" Optics Letters, vol. 27, No. 13, Jul. 1, 2002, pp. 1168-1170.
Rinia et al., "Quantitative Label Free Imaging of Lipid Composition and Packing of Individual Cellular Lipid Droplets Using Multiplex CARS Microscopy" Biophysical Journal, vol. 95, Nov. 2008, Biophysical Society, pp. 4908-4914.
Cheng et al., "Multiplex Coherent Anti-Stokes Raman Scattering Microspectroscopy and Study of Lipid Vesicles." J. Phys. Chem. B, 2002, 106, American Chemical Society, pp. 8493-8498.
Wurpel et al., "Chemical specificity in three-dimensional imaging with multiplex coherent anti-stokes Raman scattering microscopy" Optics Letters, vol. 27, No. 13, Jul. 2002, Optical Society of America, pp. 1093-1095.
Freudiger et al., "Highly specific label-free molecular imaging with spectrally tailored excitation-stimulated Raman scattering (STE-SRS) microscopy" Nature Photonics, Jan. 16, 2011, Macmillan Publishers Limited, pp. 1-7.
Pegoraro et al., "Optimally chirped multimodal CARS microscopy based on a single Ti:sapphire oscillator" Optics Express, Feb. 16, 2009, vol. 17, No. 4, Optical Society of America, pp. 2984-2996.
Hellerer et al., "Spectral focusing: High spectral resolution spectroscopy with broad-bandwidth laser pulses" Applied Physics Letters, vol. 85, No. 1, Jul. 5, 2004, American Institute of Physics, pp. 25-27.
Andrianov et al., "All-fiber design of hybrid Er-doped laser/Yb-doped amplifier system for high-power ultrashort pulse generation" Optics Letters, vol. 35, No. 22, Nov. 15, 2010, Optical Society of America, pp. 3805-3807.
Kieu et al., "High power femtosecond source near 1 micron based on an all-fiber Er-doped mode-locked laser" Optics Express, vol. 18, No. 20, Sep. 27, 2010, Optical Society of America, pp. 21350-21355.
Kieu et al., "Self-similar and Stretched-pulse Operation of Erbium-doped Fiber Lasers with Carbon Nanotubes Saturable Absorber" 2008 Optical Society of America, 2 pages.
Kieu et al., "Soliton Thulium-Doped Fiber Laser With Carbon Nanotube Saturable Absorber" IEEE Photonics Technology Letters, vol. 21, No. 3, Feb. 1, 2009, pp. 128-130.
Kieu et al., "Femtosecond laser pulse generation with a fiber taper embedded in carbon nanotube/polymer composite" Optics Letters, vol. 32, No. 15, Aug. 1, 2007, Optical Society of America, pp. 2242-2244.
Min et al., "Imaging chromophores with undetectable fluorescence by stimulated emission microscopy" vol. 461, Oct. 22, 2009, pp. 1105-1109.
Fu et al., "High-resolution in vivo imaging of blood vessels without labeling" Optics Letters, vol. 32, No. 18, Sep. 15, 2007, Optical Society of America, pp. 2641-2643.
Freudiger et al., "Label-Free Biomedical Imaging with High Sensitivity by Stimulated Raman Scattering Microscopy" Science, vol. 322, Dec. 19, 2008, pp. 1857-1861.
Zumbusch et al., "Three-Dimensional Vibrational Imaging by Coherent Anti-Stokes Raman Scattering" Physical Review Letter, vol. 82, No. 20, May 17, 1999, The American Physical Society, pp. 4142-4145.
Kieu et al., "Demonstration of Zeno switching through inverse Raman scattering in an optical fiber", Optics Express, vol. 19, No. 13, Jun. 14, 2011, Optical Society of America.
Kieu et al., "Zeno Switching Through Inverse Raman Scattering in Optical Fiber", Nonlinear Optics, p. 35, Dec. 2010.
Fermann et al., "Ultrawide tunable Er soliton fiber laser amplified in Yb-doped fiber" Optics Letters; vol. 24, No. 20, Oct. 15, 1999, Optical Society of America, pp. 1428-1430.
Imeshev et al., "230-kW peak power femtosecond pulses from a high power tunable source based on amplification in Tm-doped fiber" Optics Express, Col. 13, No. 19, Sep. 19, 2005, pp. 7424-7431.

\* cited by examiner

Input spectra

Output spectra

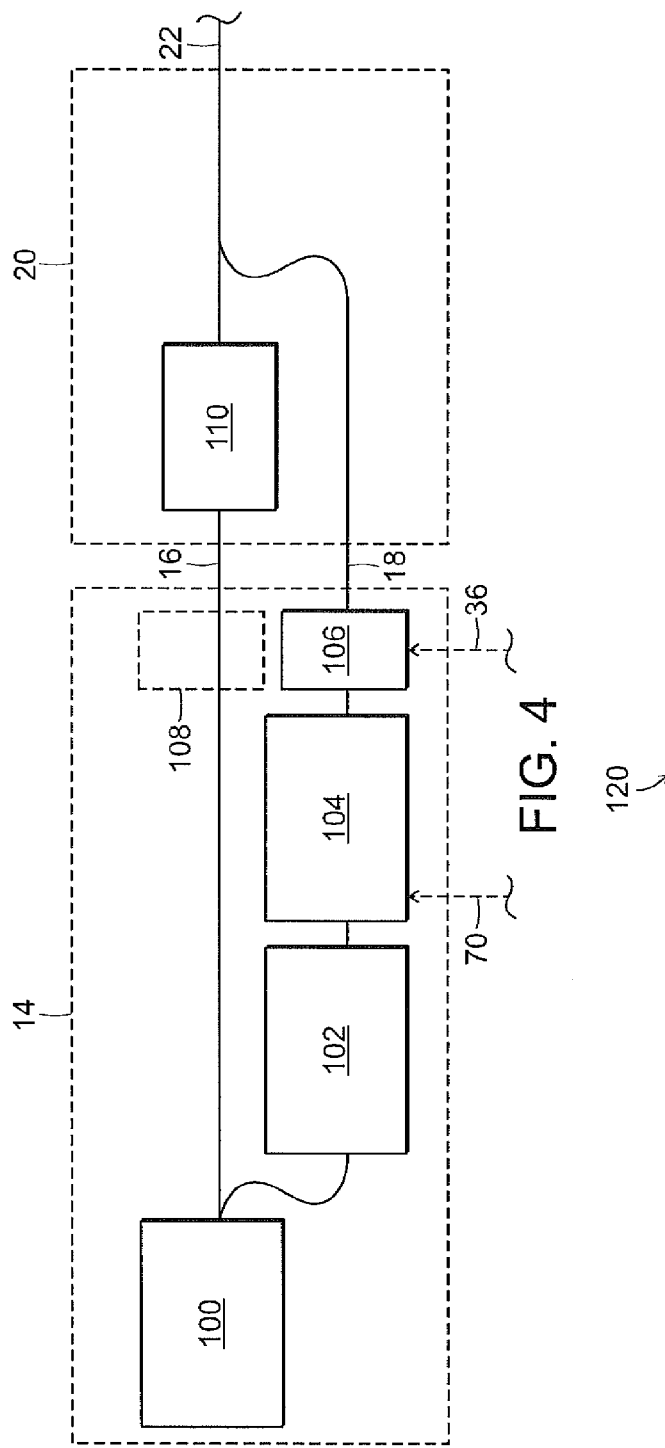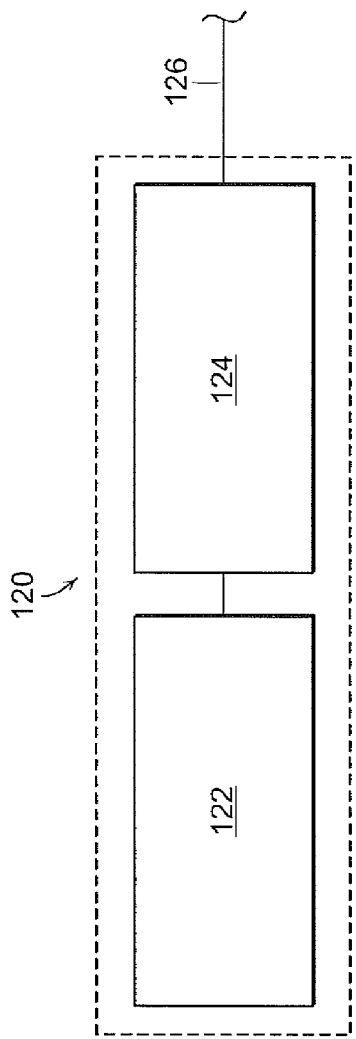

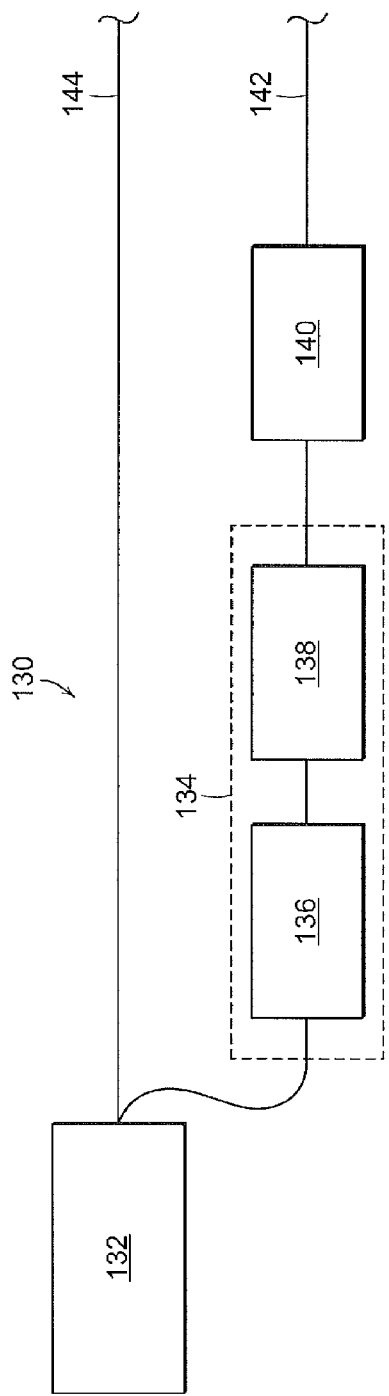
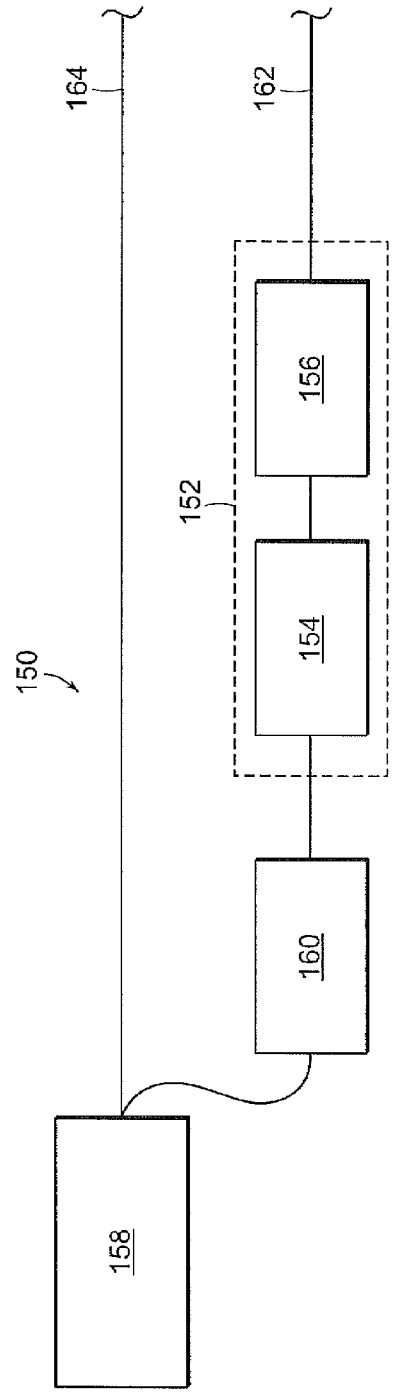

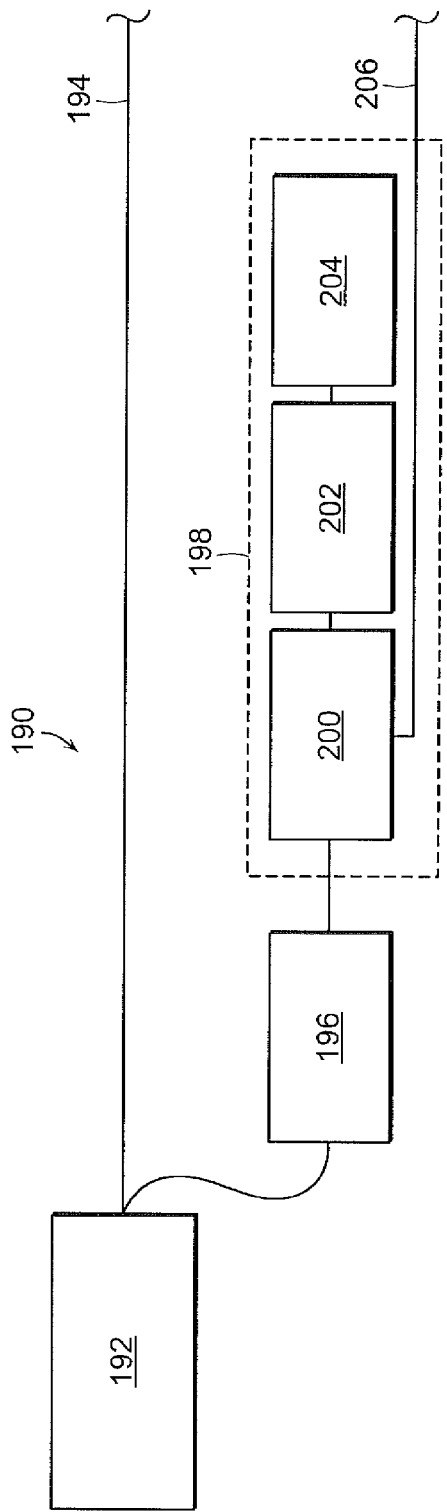
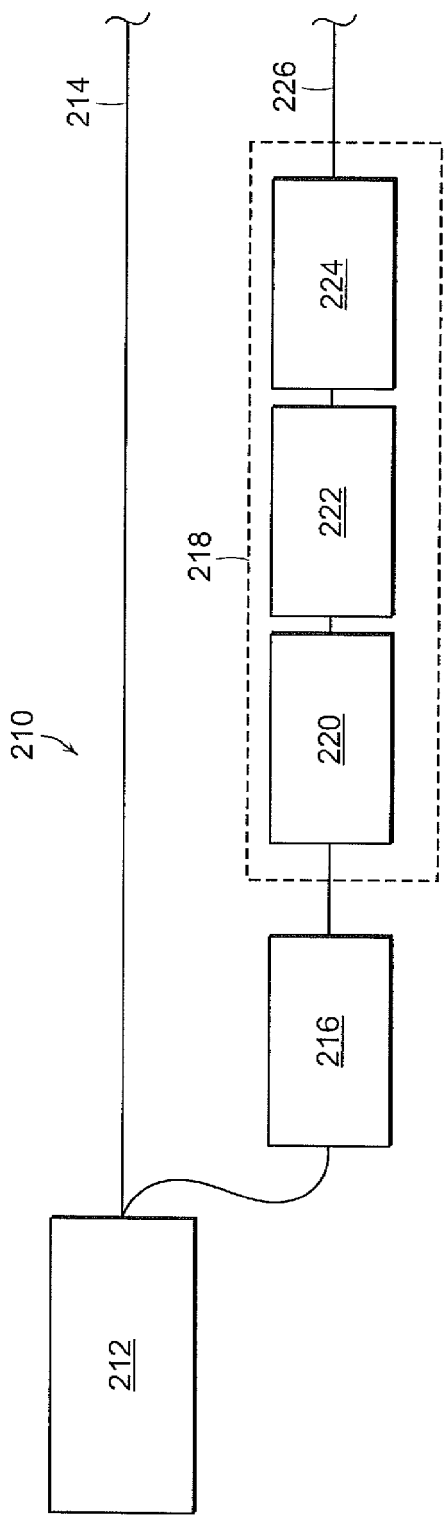

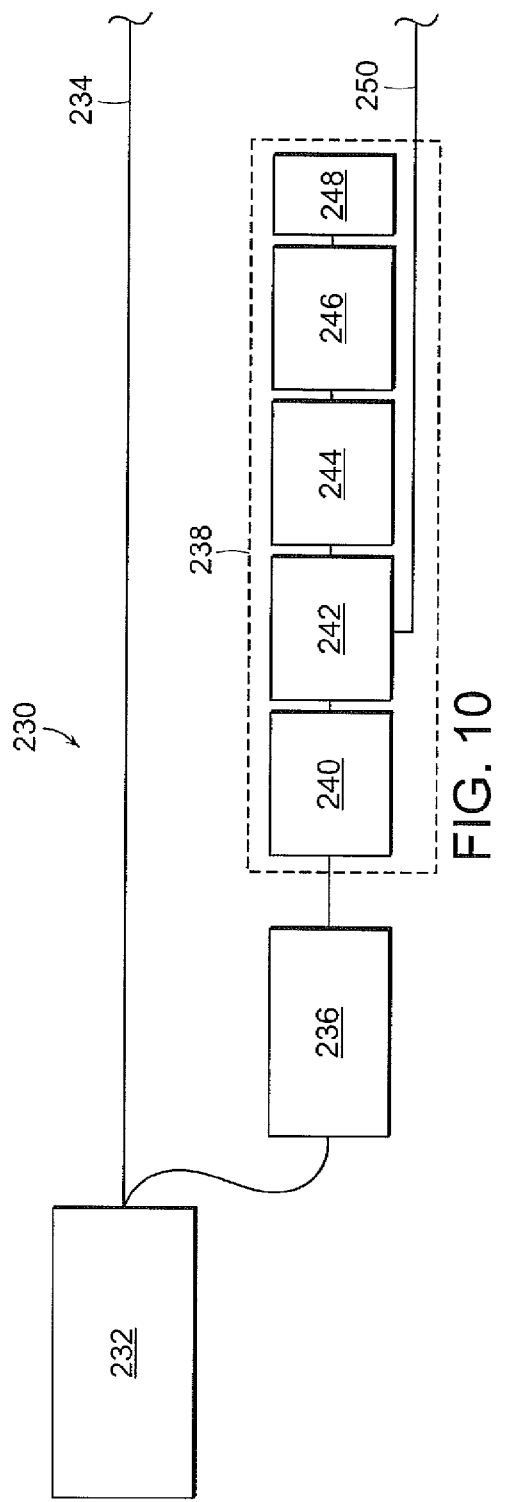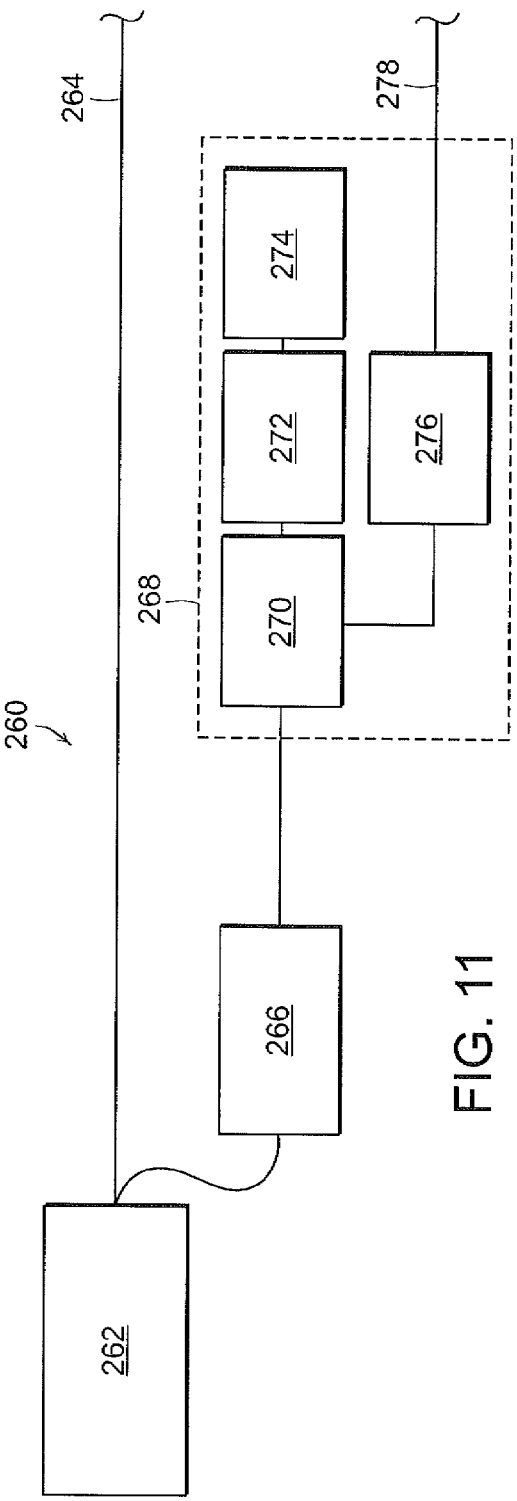

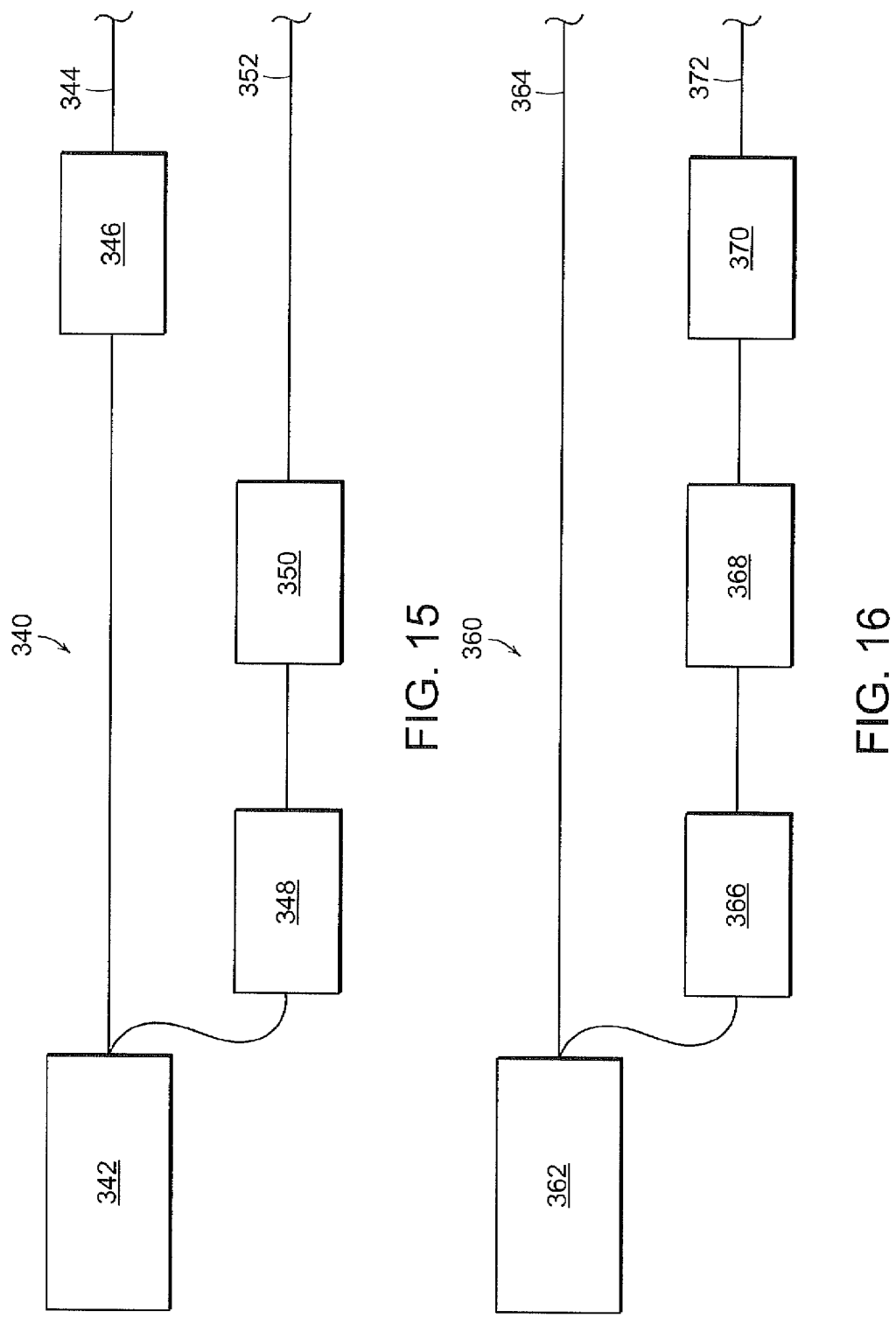

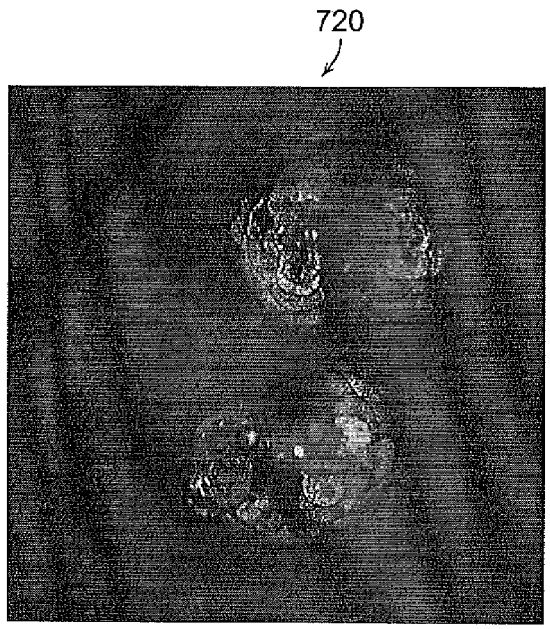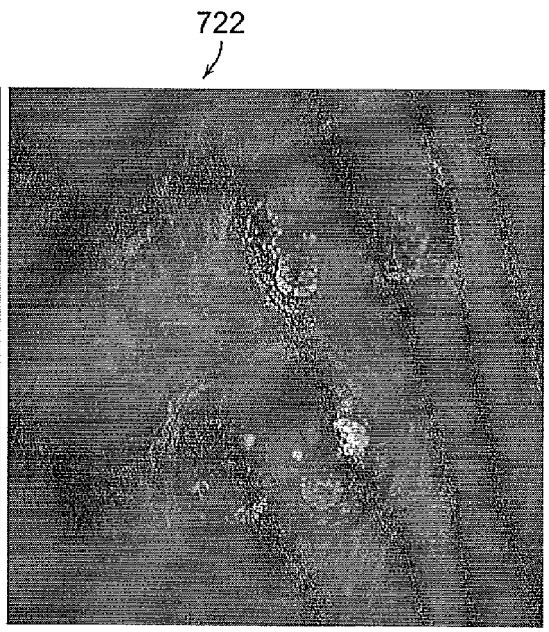
FIG. 33A  FIG. 33B
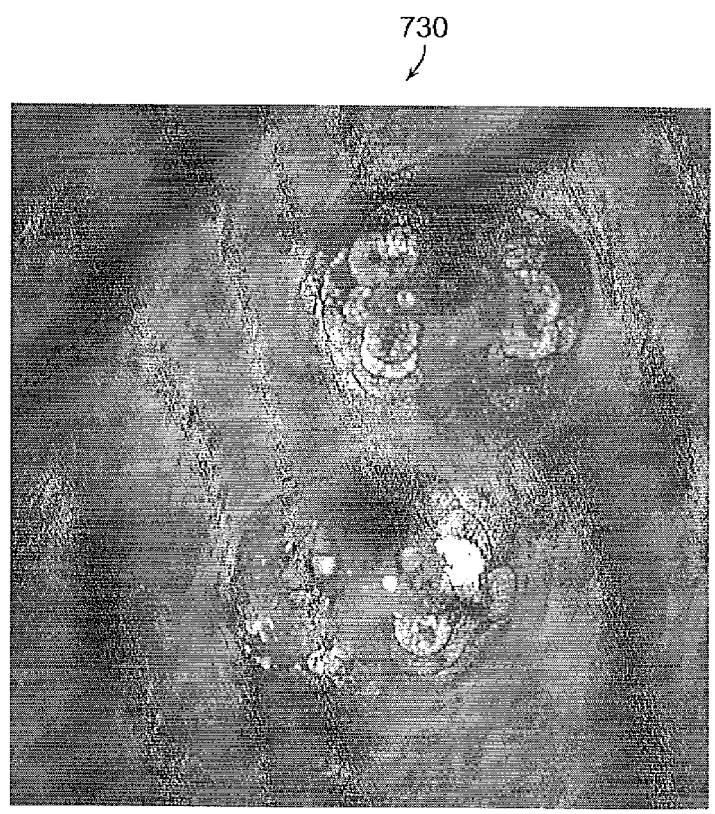
FIG. 34

LASER ILLUMINATION SYSTEMS AND METHODS FOR DUAL-EXCITATION WAVELENGTH NON-LINEAR OPTICAL MICROSCOPY AND MICRO-SPECTROSCOPY SYSTEMS

SPONSORSHIP INFORMATION

This invention was made with government support under 1R01EB010244 awarded by National Institutes of Health. The government has certain rights in the invention.

BACKGROUND

The invention generally relates to label-free imaging systems, and relates in particular to non-linear optical microscopy and micro-spectroscopy imaging systems employing efficient dual frequency laser sources.

The development of confocal microscopy and genetically encodable fluorescent labels has transformed biological research. Labels however, may be perturbative of a sample, especially for imaging molecules that are smaller than typical fluorophores (e.g., metabolites or drugs) and that are not applicable for in vivo diagnostics due to toxicity and/or delivery concerns. Certain molecules or properties (e.g., strain or stress in material science samples) cannot be labeled at all, and photobleaching may be problematic for long term measurements.

Alternatively, vibrational spectroscopy may provide label-free chemical contrast based on intrinsic molecular properties of the sample. Yet, the traditional techniques, infrared absorption (IR) and spontaneous Raman, are limited, and IR microscopy suffers from low spatial resolution and limited imaging depth due to the long wavelength. Spontaneous Raman microscopy has slow imaging speed due to the weakness of the signal.

Micro-spectroscopy generally involves capturing a spectrum from a microscopic volume in a sample, while microscopy generally involves capturing an intensity value as well as scanning such that multiple intensity values are captured to form picture elements (pixels) of a microscopy image.

Infrared microscopy involves directly measuring the absorption of vibrationally excited states in a sample, but such infrared microscopy is generally limited by poor spatial resolution due to the long wavelength of infrared light, as well as by a low penetration depth due to a strong infrared light absorption by the water in biological samples.

Raman microscopy records the spontaneous inelastic Raman scattering upon a single (ultraviolet, visible or near infrared) continuous wave (CW) laser excitation. Raman microscopy has improved optical resolution and penetration depth as compared to infrared microscopy, but the sensitivity of Raman microscopy is rather poor because of the very low spontaneous Raman scattering efficiency (Raman scattering cross section is typically on the order of $10^{-30}$ cm$^2$). This results in long averaging times per image, which limits the biomedical application of Raman microscopy.

Coherent Raman scattering (CRS) microscopy techniques, including coherent anti-Stokes Raman scattering (CARS) microscopy and stimulated Raman scattering (SRS) microscopy allow signal amplification by up 100,000× compared to spontaneous Raman, enabling label-free imaging with high temporal (imaging speeds up to video-rate, i.e., 30 frames/s) and sub-micron spatial resolution. Due to the use of nonlinear excitation, CRS microscopy is intrinsically three-dimensional, allowing non-destructive optical sectioning of the sample. The excitation uses near-infrared light within the optical window of biological specimen, allowing imaging depths up to a few hundred microns.

CRS is also free of photobleaching, if electronic resonances are avoided; and auto-fluorescence does not interfere, because it is not coherently amplified. CRS imaging systems may be used in biology and material science research, such as studying lipid metabolism, optimizing drug formulation for trans-dermal delivery, and in biofuel production. Label-free microscopy is also being evaluated as a medical imaging modality for delineation of tumor margins in brain and breast cancer surgery and early detection of melanoma.

Despite the advantages of CRS, high instrument cost and the technical complexity limit its wider use and currently only a few laboratories can obtain high quality images. Providing laser sources for CRS is challenging not only due to the comparative cost of laser systems as compared to a complete conventional Raman system, but the illumination must be provided as two synchronized laser pulse-trains of picosecond pulse duration, with a tunable difference frequency to the precision of a typical Raman line width.

Modulation transfer microscopy and spectroscopy imaging systems such as stimulated Raman scattering (SRS), spectral excitation of stimulated Raman scattering (SRS Spectral), stimulated emission (SE), ground state depletion (GD), photo-thermal (PT), two-color two-photon absorption (TPA), and stimulated Brillouin scattering generally involve reliance on the non-linear interaction of two laser beams within a sample, and detection of a characteristic, such as gain or loss, of one of the excitation beams. This is in contrast to detecting a newly generated (new frequency) emission signal as is done, for example, in one-photon and two-photon excited fluorescence, spontaneous Raman scattering, coherent anti-Stokes Raman scattering (CARS), second harmonic generation, (SHG), sum frequency generation (SFG) and third harmonic generation (THG).

Such modulation transfer microscopy and micro-spectroscopy techniques require a detection scheme that provides for detection of a relatively small signal (e.g., a small gain and loss signal) on top of noisy lasers. This is generally achieved in accordance with various embodiments based on modulation transfer—by modulating a feature of one of the laser excitation beams and measuring the signal of interest with high sensitivity. In particular, the modulation transfers to the other excitation beam due to non-linear interaction within the sample, which facilitates detection of the signal of interest using a modulation sensitive detector. If the modulation frequency is chosen to be faster than the laser noise (e.g., greater than about 200 kHz), shot-noise limited sensitivity may be achieved. Such modulation schemes are readily compatible with beam-scanning microscopy and micro-endoscopy, video-rate imaging speeds, and multiplex excitation schemes.

An advantage of these non-linear optical imaging techniques as compared to fluorescence microscopy, is that they allow for specific image contrast based on intrinsic spectroscopic properties of the sample, rather than extrinsic fluorescent labeling or dye staining. This is particularly important for imaging of small molecules that can be perturbed by labeling and medical diagnostics because of a possible toxicity of the used dyes. In CARS and SRS, chemical contrast is derived from intrinsic molecular vibrations and in TPA, SE and GD microscopy from absorption properties of the molecules constituting the sample.

Common features of CARS and SRS include that each requires (1) pulsed laser beams with a pulse-width shorter than about 10 ps, i.e., a spectral bandwidth of at least about 30 GHz, and (2) two synchronized beams that are overlapped in time.

Modulation transfer techniques further require that a property (such as intensity, polarization or time delay) of one of the beams is modulated at a rate higher than 100 kHz allowing measurement the modulation transfer from this modulated beam to the second, originally un-modulated beam due to the nonlinear interaction in the sample These different techniques have different laser wavelength requirements. For CARS an SRS, the difference between the two excitation frequencies ($|\omega_1-\omega_2|$) is selected to be resonant with a vibrational frequency of the sample. The specific wavelengths of the two excitation fields, therefore are not critical as long as the difference frequency is as desired. Such sources are typically chosen to be in the range of about 700 nm to about 1600 nm, for which biological samples are transparent. The tuning of the difference frequency to a vibrational frequency of the sample (about 200 $cm^{-1}$ to about 4000 $cm^{-1}$) should be to a precision of at least about 2 nm.

Stimulated emission (SE) and ground state depletion (GD) microscopy involve tuning either $\omega_1$ or $\omega_2$ to be electronically resonant with the sample. With photo-thermal (PT) microscopy, either $\omega_1$ or $\omega_2$ is chosen to match the one or two photon electronic absorption frequency. With two-color two-photon absorption (TPA), the sum of $\omega_1$ and $\omega_2$ is chosen to be electronically resonant with the sample.

Many conventional laser systems for CARS and MTM techniques have involved the use of mode-locked solid state lasers in order to achieve the pulse width shorter than 10 ps as such pulse-width that cannot conventionally be achieved with an electrically driven laser systems. A particular challenge, is the requirement of overlaps the pulses in time precisely (synchronization), as timing jitter translates into severe noise of the signal if it is bigger than the pulse width (i.e., much smaller than the required 10 ps).

Certain conventional implementations of CARS microscopy involved using two Titanium Sapphire (Ti:Sa) lasers whose outputs were electronically locked to one another using feedback regarding the cavity length of one of the lasers. Both Ti:Sa lasers were continuously tunable from about 750 nm-1000 nm, which allowed imaging based on Raman frequencies in the entire spectral region from about 200 $cm^{-1}$-4000 $cm^{-1}$. Such systems however, suffered from timing jitter between the pulses, making long-term experiments impossible and limiting day-to-day stability of the system.

Later developed conventional system involved the use of optical parametric oscillators (OPO) for label-free microscopy that are intrinsically locked due to synchronously pumping the OPO with the same lasers that provides the first beam. Such OPO laser systems may also be pumped with made-locked fiber lasers. The pump laser is typically fixed at 1064 nm and the OPO output is tunable from 750 nm to 1000 nm, again allowing to image any Raman band. The long-term stability, complexity and price of such OPO laser systems however, remains a shortcoming of such systems. Moreover, dual frequency sources employing OPO laser systems typically include an adjustable translation stage that ensures that the resulting two trains of laser pulses are temporally overlapped. Such an adjustable translation stage adjusts the optical path of one of the pulse trains within a short range to ensure temporal synchronicity. Variations in temperature of the imaging system will also affect the path lengths and therefore synchronization.

Another approach to providing illumination systems for dual-excitation wavelength non-linear imaging systems has been based on time-lens lasers, which allow generation of pulses on demand with response to an electronic trigger signal. A Yb time-lens laser may be triggered by a Ti:Sa laser to provide to laser pulse trains for CRS with minimal timing jitter. One wavelength is fixed at 1040 nm and the other is tunable over the entire region of Raman spectra. Again however, the synchronization of the two oscillators is achieved electronically rather than by optical seeding.

Other approaches to providing laser pulse trains for CRS have been based on super-continuum generation (SC) in an optical fiber to generate a frequency shifted second train of pulses synchronized to the first train of pulses. Typically SC spectra are very broad, much more broad than the typical line-shape of Raman spectra and SC light sources for CRS are combined with spectral compression schemes to recover the chemical specificity of CRS. This may be achieved either by spectral focusing CRS or by spectral compression via sum frequency generation.

This permits the generation of the spectral brightness required for CRS imaging and allows for fast imaging speed with pixel dwell times as short as 4 μs. Because Raman SC spectra are very broad, SC light sources are broadly tunable (e.g., from 850 nm-1100 nm) and allow access Raman peaks across the full Raman spectrum. While relying on optical synchronization, this approach is different from the laser system disclosed herein in that the second pulse train is generated by super continuum generation in a nonlinear fiber rather than lasing; In the nonlinear fiber, the molecular population is unaffected similar to the parametric process in OPOs.

Ultrafast laser systems have also been disclosed based on seeding a Yb-doped amplified with a super-continuum generated from an Er-doped oscillator. Such systems however, only provide a single-color output, which is not suitable for CRS microscopy, which SRS requires the generation of two synchronized trains of picosecond pulses with narrow bandwidth (a few cm-1) and that are independently tunable over a wide spectral range 800-3300 cm-1. Further, they are intrinsically broadband due to the broad spectral range from the super-continuum fiber that directly seeds the amplifier.

There remains a need, therefore, for an efficient dual frequency laser system with reduced jitter for microscopy and micro-spectroscopy imaging systems.

SUMMARY

In accordance with an embodiment, the invention provides an illumination system for providing dual-excitation wavelength illumination for non-linear optical microscopy and micro-spectroscopy. The illumination system includes a laser system, an optical splitting means, a frequency shifting system, and a picosecond amplifier system. The laser system includes a laser for providing a first train of pulses at a center optical frequency $\omega_1$. The optical splitting means divides the first train of pulses at the center optical frequency $\omega_1$ into two trains of pulses. The frequency shifting system shifts the optical frequency of one of the two trains of pulses to provide a frequency shifted train of pulses. The picosecond amplifier system amplifies the frequency shifted train of pulses to provide an amplified frequency-shifted train of pulses having a pulse duration of at least 0.5 picoseconds. In accordance with further embodiments, the picosecond amplifier system may be a narrowband amplifier system or a chirped amplifier system.

In accordance with another embodiment, the invention provides an illumination system includes a laser system, an optical splitting means, a frequency shifting system, an amplifier system, and combining means. The amplifier system is for amplifying the frequency-shifted train of pulses to provide an amplified frequency-shifted train of pulses, and the combining means is for combining the amplified frequency-shifted train of pulses with a second of the two trains of laser pulses from the optical splitting means to provide the amplified frequency-shifted train of pulses and the second of the two trains of laser pulses from the optical splitting means as a collinear train of laser pulses for the dual-excitation wavelength illumination In further embodiments, the illumination system is provided in a dual-excitation wavelength nonlinear Stimulated Raman Scattering microscopy or two-color two-photon microscopy system.

In accordance with a further embodiment, the invention provides a method of providing dual-excitation wavelength illumination for non-linear optical microscopy and microspectroscopy. The method includes the steps of providing a first train of pulses at a center optical frequency $\omega_1$ using a laser oscillator; dividing the first train of pulses at the center optical frequency $\omega_1$ into a first split train of pulses and a second split train of pulses; shifting the optical frequency of the first split train of pulses to provide a frequency shifted train of pulses; and amplifying the frequency shifted train of pulses to provide a amplified frequency-shifted train of pulses having a pulse duration of at least 0.5 picoseconds.

BRIEF DESCRIPTION OF THE DRAWINGS

The following description may be further understood with reference to the accompanying drawings in which:

FIG. 4 shows an illustrative diagrammatic view of a an illumination system in accordance with an embodiment of the invention;

FIG. 5 shows an illustrative diagrammatic view of a an laser system for use in the illumination system of FIG. 4 in accordance with an embodiment of the invention;

FIG. 6 shows a illustrative diagrammatic view of a portion of the illumination system of FIG. 4 employing a frequency shifting system in accordance with an embodiment of the invention;

FIG. 7 shows a illustrative diagrammatic view of a portion of the illumination system of FIG. 4 employing a further frequency shifting system in accordance with another embodiment of the invention;

FIGS. 8-11 show illustrative diagrammatic views of a portion of the illumination system of FIG. 4 employing further narrowband amplifier systems in accordance with further embodiments of the invention;

FIGS. 15-16 show illustrative diagrammatic views of a portion of the illumination system of FIG. 4 employing frequency doubling/tripling units in accordance with further embodiments of the invention;

FIGS. 33A and 33B show illustrative photographic representations of CH2 vibrations (lipids) obtained using an illumination system of the present invention and of CH3-vibrations (proteins) obtained using an illumination system of the present invention; and FIG. 34 shows an illustrative graphical representation of an image for sebaceous land in a subject.

The drawings are shown for illustrative purposes only.

DETAILED DESCRIPTION

The promise of label-free microscopy is that one may obtain rich, chemical specific contrast based on intrinsic properties of the sample. As each type of chemical bond has a specific stiffness (e.g., C=C is stiffer than C—C) and associated mass (e.g., C—C is heavier than C—H), it has a characteristic vibrational frequency $\Omega$. Vibrational spectra of the sample, which consist of the vibrational frequencies of the molecule, provide a unique molecular fingerprint. Raman scattering is an elegant way to measure vibrational spectra with visible light. When a molecule is excited (de-excited), an incident photon is annihilated a new red-shifted (blue-shifted) photon is generated at the Stokes (anti-Stokes) frequency $\omega_S=\omega_P-\Omega$ (and $\omega_{AS}=\omega_P+\Omega$) due to energy conservation. The emission spectra, $\sigma(\Omega)=\sigma(\omega_P-\omega_S)$, can be measured by dispersing the light on a spectrometer.

In a specific implementation, the invention provides an ultrafast dual-excitation wavelength laser source based on a fiber laser technology. Because light is guided within the optical fiber, misalignment is impossible. Existing fiber-lasers do not, however, reach the same performance level of free-space systems in CRS. An important realization is that the difference frequency of the two most common fiber gain media, erbium (Er) and ytterbium (Yb), coincides with the high-wavenumber region of Raman spectra, where most CRS microscopy is performed. The invention provides an all-fiber system based on optical synchronization of Er- and Yb-doped power amplifiers via super-continuum seeding and careful control the pulse properties for CRS microscopy.

Figure 1:
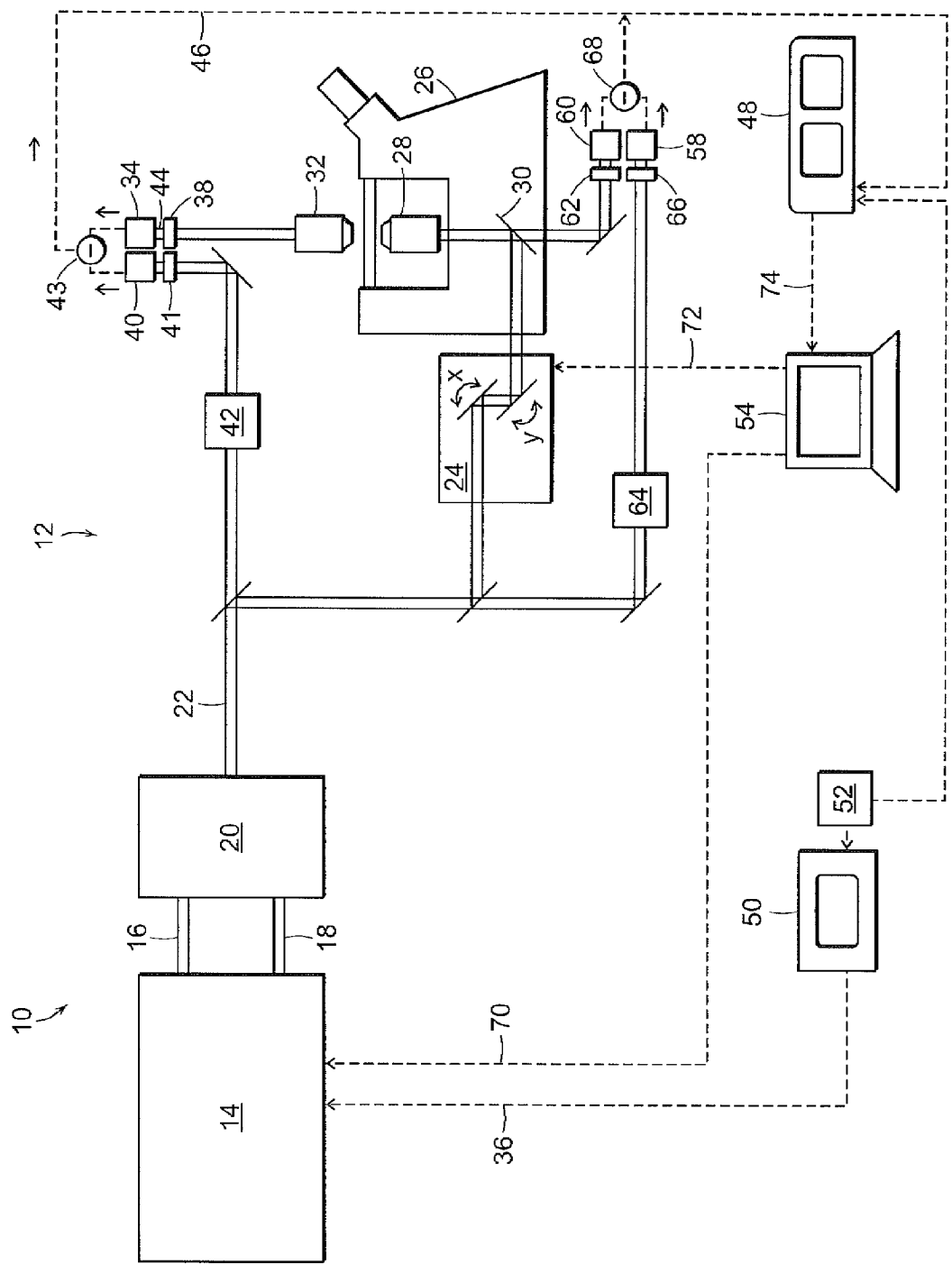
FIG. 1 shows an illustrative diagrammatic view of an illumination system and imaging system employing a dual-frequency source in accordance with an embodiment of the invention.

FIG. 1 shows an illumination system 10 in accordance with an embodiment of the invention together with a microscopy imaging system 12. The illumination system 10 includes a laser system 14 (that provides two trains of laser pulses 16, 18) and a combiner system 20 that combines the two trains of laser pulses such that they are collinear and spatially and temporally overlapped. One of the trains of laser pulses 16 is at a center frequency $\omega_1$ (e.g., a Stokes frequency of about 1030 nm), and the other train of laser pulses 18 is at a different center frequency (e.g., 800 nm).

The combined trains of laser pulses 22 are directed via a scanhead 24 (that scans in mutually orthogonal x and y directions), into a microscope 26 that includes optics 28 that direct and focus the combined trains of laser pulses into the focal volume, e.g., via a mirror 30. The illumination from the focal volume is directed by a condenser 32 onto an optical detector 34. One of the trains of laser pulses 16 or 18 (a first train of laser pulses) is modulated within the laser system responsive to a modulation signal 36, and, at the detector 34 the modulated first beam (e.g., the Stokes beam) is blocked by an optical filter 38. The optical detector 34, such as a photodiode, therefore measures the intensity of the other (second) beam (e.g., the pump beam) only.

The system may further include balanced detectors. In particular, another optical detector 40 may be employed with a filter 41 such that the detector 40 only sees the original pump or Stokes beam that was not modulated. The difference between the outputs of these detectors 34 and 44 is provided by a subtraction unit 43, which outputs the output electrical signal 46. A delay unit 42 permits adjustment of the timing of the original second train of laser pulses. An electrical output signal 46 is provided to a signal processor 48.

The first train of laser pulses is modulated at modulation frequency f, by a modulation system that includes, for example, a modulator within the laser system as discussed in further detail below, a controller 50, and a modulation source 52. The modulation source provides a common modulation control signal to the controller 50 as well as to a signal processor 48. The integrated intensity of substantially all frequency components of the second train of laser pulses from the optical detector 34 is provided to the signal processor 48, and the modulation (amplitude and/or phase) of the integrated intensity of substantially all the optical frequency components of the second train of laser pulses due to the non-linear interaction of the first and second trains of laser pulses in the focal volume is detected at the modulation frequency f to provide a pixel of an image to a microscopy control computer 54. The microscopy control computer 54 is employed as an imaging system, and further provides user control of the scanhead 24 as shown at 56.

In a further embodiment, an epi-directed detection scheme may be employed wherein the illumination from the focal volume is received back through the optics 28 and passes through a filter 62 to a detector 60 that provides an electrical output signal to a subtraction unit 68. The subtraction unit 68 also receives an output signal from a detector 58 via a filter 66 that receives the original pump or Stokes beam that was not modulated. Again, a delay unit 64 permits adjustment of the timing of the original second train of laser pulses. The use of the second detector and the subtraction unit provides that any laser background noise as well as any low frequency variations in the laser power, will be removed from the detected signal, (whether detected in the forward or epi direction).

Tuning control of the lasers output trains may also be provided using the microscopy control computer 54 that directs a control signal 70 to the laser system 14 as shown. Such tuning control may control the frequency difference between the pump and Stokes beams to provide for tuning into different compositions in the sample. Coupled with the ability to scan the excitation fields (as shown at 74), the control computer 54 may then direct the microscopy system to scan an area for a variety of different compositions, and the resulting pixel data is provided (as shown at 74) to the control computer 54.

The modulation system may provide amplitude modulation of the first beam to provide a modulated pulse train such that only alternating pulses of the first pulse train are coincident with the pulses of the second pulse train. Such amplitude modulation of the first beam may be achieved using a Pockel cell and polarization analyzer as the modulator, and a Pockel cell driver as the controller.

If the modulation rate is of the same order of the repetition rate of the laser, countdown electronics must be utilized to guarantee the synchronization (phase) between the modulation and the pulse train. A wide variety of different modulation rates are also possible. In further embodiments, the contrast pulses may have an amplitude that is substantially zero by switching off the pulses at the modulation frequency, for example using an electro-optic modulator (such as a MEMs device or a galvanometric scanner) or an acousto-optic modulator.

Amplitude modulation of the pump or Stokes pulse trains may therefore be achieved, and the increase of the Stokes pulse train or decrease of the pump pulse train may be measured. By modulating the pump train of pulses and then detecting the Stokes train of pulses from the focal volume, Raman gain may be determined by the processing system. In an embodiment, the pump beam may be modulated, the Stokes beam may be detected from the focal volume, and Raman gain may be determined by the processing system. In a further embodiment, the Stokes beam may be modulated, the pump beam may be detected from the focal volume, and Raman loss may be determined by the processing system.

In spontaneous Raman scattering, the sample is excited with light at a single frequency $\omega_p$. The output spectrum contains new radiation on both the Stokes ($\omega_S$) and anti-Stokes sides ($\omega_{nS}$) due to inelastic light scattering off molecular vibrations. In CRS, the combined action of pump and Stokes beams effectively transfers the molecules in the sample from the ground state into the targeted vibrational state. As a consequence a pump photon is absorbed and a Stokes photon is generated. This allows signal amplification by up 100,000× compared to spontaneous Raman scattering.

In contrast to fluorescence, the energy of the incident photons typically does not match an electronic excited state, and spontaneous Raman scattering is mediated through a virtual state rather than an excited electronic state, relying on vacuum fluctuations to generate the new emission. As such, spontaneous Raman scattering is extremely weak, resulting in long averaging times to obtain high signal to noise ratio (SNR) spectra and slow imaging speed in microscopy.

In CRS the sample is excited with two laser beams. The difference frequency, $\Delta\omega=\omega_P-\omega_S$, is tuned to match the frequency of a target vibration, $\Omega$. In this case, the transition from the virtual state into the vibrational excited state is stimulated, not spontaneous, similar to the well-known phenomena of stimulated emission, which allows for light amplification in lasers. The molecular transition rate is consequently enhanced by $r_{coh}/r_{spo}=n_{Stokes}+1$, where $n_{Stokes}$ corresponds to the number of photons in the optical mode of the Stokes beam and the +1 indicates spontaneous transitions. This is the origin for signal enhancement in CRS and the basis of fast label-free imaging. Ultimately $n_{Stokes}$ and thus enhancement is limited by photodamage to ~100,000× in biological specimen. This means that a complete high-resolution imaged may be acquired with CRS in the same time as a single spectrum with spontaneous Raman. Optimization of the laser parameters enables for high sensitivity and imaging speeds up to video-rate.

The two most popular CRS techniques, CARS and SRS, share this common excitation scheme and are, in fact, excited simultaneously. They differ in the detection. The CARS signal at the anti-Stokes frequency is detected by blocking the excitation beam with a high optical density (OD) filter after the sample. SRS, comprising stimulated Raman gain (SRG) of the Stokes beam and stimulated Raman loss (SRL) of the pump beam, are the intensity variations ΔI of the excitation beams I associated with the energy transfer from the optical field to the sample. Under biomedical excitation condition, the relative changes are however small ($\Delta I/I < 10^{-4}$) and can be buried in the intensity fluctuations of the excitation lasers or the linear absorption or scattering of the sample.

A high-frequency modulation/detection scheme has therefore been developed to extract the SRS signal with high sensitivity as disclosed, for example, in U.S. Pat. No. 8,027,032, the disclosure of which is hereby incorporated by reference in its entirety. SRS is more sensitive than CARS, linear in the concentration of the target molecule and free from artifacts due to phase-matching. Detection is, however, somewhat more challenging. In particular, signal detection in reflection of thick, non-transparent samples (epi-detection) is more straight forward with CARS. As CARS and SRS share the same excitation conditions, the illumination systems of the present invention are applicable to both CRS techniques.

Figure 2A:
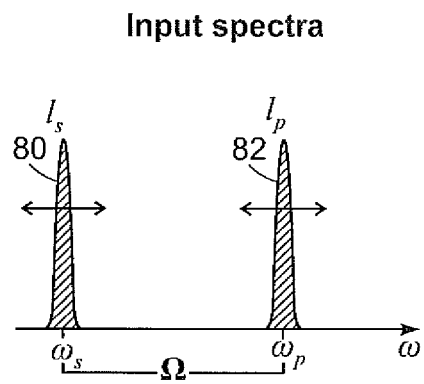
FIGS. 2A and 2B show illustrative diagrammatic views of narrowband excitation and output spectra in an SRS system in accordance with an embodiment of the present invention.
Figure 2B:
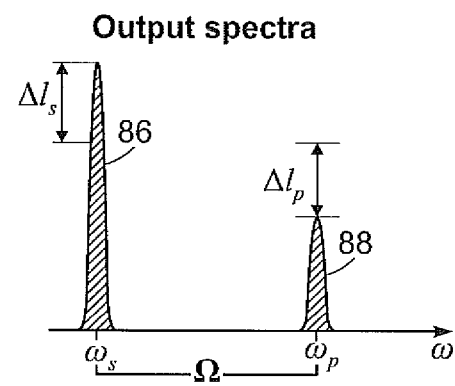

The input trains of laser pulses should be narowband (with a pulse that is longer than 0.5 ps). With reference to FIG. 2A both of the two synchronized trains of laser pulses 80, 82, may be narrowband pulses, and as shown at 86 and 88, the increase in intensity of the Stokes illumination ($\Delta I_S$) may be detected or the decrease in the pump illumination ($\Delta I_p$) may be detected. As also shown in FIG. 2B, $\omega_p - \omega_S = \Omega$. When both are narrowband, the difference frequency has to be adjusted, for example, by tuning either of the two center frequencies.

For CRS, the illumination system 10 should provide the two trains of laser pulses $\omega_p$ and $\omega_S$, one of which is modulated, and CRS occurs as long as $\Delta\omega = \omega_p - \omega_S$ falls within the linewidth, typically ~20 cm$^{-1}$ (at 800 nm, 20 cm$^{-1}$=1.3 nm) of a Raman transition. As a consequence, a CRS laser source has to fulfill the following requirements. First, at least one of the laser beams has to be tunable to a precision narrower than about 0.2 nm. Second, the laser bandwidth has to be narrower than the typical Raman line-width (<3 nm). Third, the absolute wavelength is not critical, in contrast to spontaneous Raman scattering, which scales with $1/\lambda^4$. For biological samples however, it is advantages to excite the sample in the optical window from 700-1300 nm, where both scattering and absorption are minimal and resolution with a high numerical aperture (NA) lens is sub-cellular.

Achieving maximal sensitivity is a primary challenge for CRS microscopy. This is where most laser systems that fulfill the first and third criteria above fail. It is critical to consider the signal-to-noise-ratio (SNR) for various laser parameters.

For continuous wave (CW) lasers, the SRS signal is proportional to the product of the average power of the pump and Stokes beams, i.e., SRS signal is nonlinear in the overall excitation power.

It is therefore advantageous to utilize pulsed lasers, which have high peak powers but moderate average powers to minimize heating effects in the sample due to linear absorption. For pulsed lasers with average power $\hat{I}_{p,S}$, pulse duration duration τ and repetition rate R, SRS signal is proportional to the following:

$$(\hat{I}_p/\tau \cdot R)\cdot(\hat{I}_S/\tau \cdot R)\cdot \tau \cdot R = \hat{I}_p \cdot \hat{I}_S/\tau \cdot R$$

High-frequency, phase-sensitive detection of SRS is close to shot-noise limited, i.e. noise for SRL is proportional to $\hat{I}_p^{0.5}$ and SNR $\propto \hat{I}_S \cdot \hat{I}_p^{0.5}/\tau \cdot R$. For a fixed total average power $\hat{I}$ at the sample, it is thus advantageous to chose $\hat{I}_S$ such that $$\hat{I}_S = 2\hat{I}_p = \frac{2}{3}\hat{I}$$

in order to maximize the SNR. A similar argument can be made for CARS microscopy, and it can be shown that for CRS microscopy, SNR $\propto \hat{I}^{1.5}/\tau \cdot R$.

The use of a low repetition rate, femtosecond laser system would maximise the SNR, but a hard limit exists however, on the repetition rate for fast microscopy, that is set to R>10 MHz (and R>40 MHz for videorate imaging) by the fact that at least one laser pulse is required per pixel (and more if the laser repetition rate is not synchronized to of the pixel clock of the microscope). The pulse duration is limited by the time-bandwidth product, which states that a laser pulse of a given duration can only be achieved if it has a certain spectral bandwidth. Requirement (B) limits τ>0.5 ps. This requirement differentiates CRS from two-photon fluorescence, which is typically excited with femtosecond (fs) lasers.

Further, it is also important to consider the damage threshold of the sample. Optimizing the sensitivity for CRS means designing the CRS laser system to approach the damage threshold. While absolute quantification of photodamage is sample and metric dependent, studies suggest that near-IR laser damage in biological samples is primarily due to nonlinear absorption phenomena with a scaling of $I_{ave}^{\gamma}/(\tau \cdot R)^{\gamma-1}$ and nonlinear scaling parameter γ being in the range from 2.5 to 3.5. The approximate measurements carried out with R=80 MHz, NA=1.2 and $\lambda_{pump}$=817 nm and Stokes $\lambda_{Stokes}$=1064 nm, indicate that the sample shows morphological changes after a single scan (the most drastic form of damage) for $\hat{I}$=25 mW at 180 fs, $\hat{I}$=80 mW at 1 ps, and $\hat{I}$=280 mW at bps. This suggests that γ≈3.2, i.e. the photodamage is more nonlinear than the CRS SNR. The maximal average power can thus be estimated by the experimental equation:

$$\hat{I}^{max} \approx 25 \text{ mW} \cdot (\tau/180fs \cdot R/80 \text{ MHz})^{\frac{3.2-1}{3.2}} \approx$$
$$25 \text{ mW} \cdot (\tau/180fs \cdot R/80 \text{ mHz})^{0.7}$$

With the above assumptions, simulations were provided to determine the best pulse properties for CRS. It has been found that and found that within the hard limits (τ=1 ps-10 ps and R>20 MHz), the CRS SNR hardly varies with the exact parameter order to achieve the same signal with a 10-ps rather than 1-ps laser pulse however, the average power requirements of the laser system is increased ~5×. Ideally the user can specify the system depending on whether it is to be optimized for high spectral resolution (i.e., larger τ and higher Î) or low average power, as for medical applications (i.e., shorter τ, lower R, and lower Î).

Figure 3A:
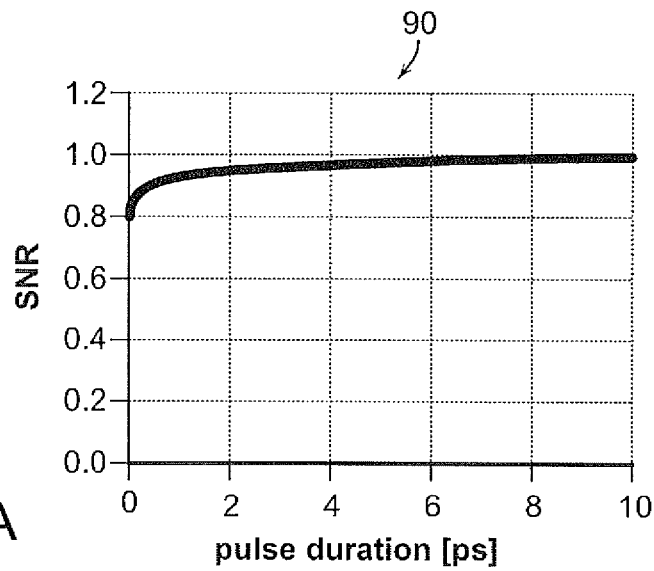
FIGS. 3A and 3B show illustrative graphical representations of estimated signal to noise ratios and required average power requirements respectively for pulse parameters in a CRS system.
Figure 3B:
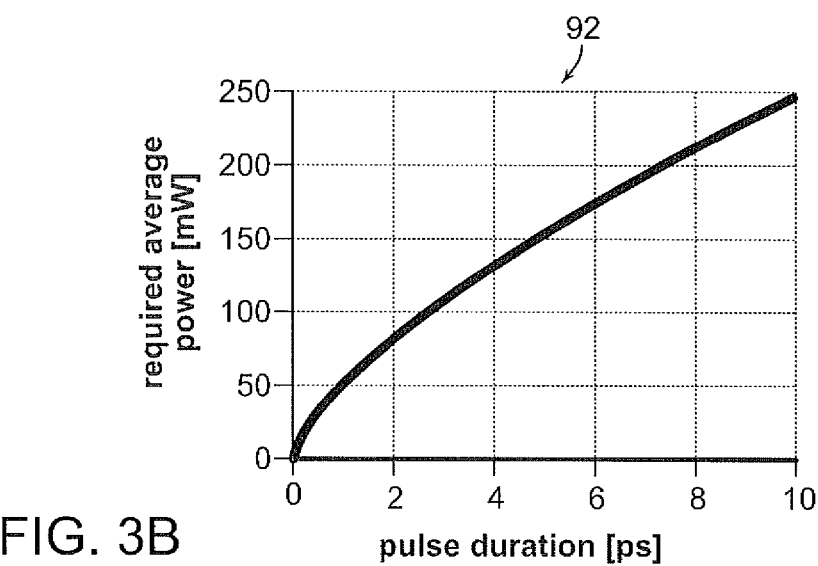

FIG. 3A shows at 90 an estimated SNR as a function of pulse duration at a fixed repletion rate of 40 MHz and normalized to SNR for excitation with 80 HMz, 6 ps pulses. This assumes excitation with maximal average power that does not cause photo-damage, and neglects effects due to limited Raman line-width. FIG. 3B shows at 92 an average power requirement for the laser system to achieve maximal SNR.

In summary, an ideal CRS laser system further requires a pulsed laser with pulse duration of 0.5-10 ps, repetition rate of 20-100 MHz, and sufficient average power given a certain pulse duration and repetition rate (FIG. 2B), as well as temporal synchronization of the pulse trains to a fraction of the pulse duration to avoid intensity fluctuations due to timing jitter.

In addition to the narrowband approach based on picosecond (ps) lasers, other modes of CRS microscopy are being investigated. A technique known as spectral focusing uses broadband frequency-chirped pulses, i.e., laser pulses with a center frequency that varies over time. If the chirp rate of both pump and Stokes pulses are matched, the frequency difference does not vary and is effectively narrowband, even though the absolute frequency is swept. Tuning the time delay changes the difference frequency, allowing different Raman peaks to be targeted. Spectral focusing is attractive for fast and reproducible spectral tuning or frequency modulation schemes.

Other approaches are based on exciting multiple vibrations simultaneously. In multiplex CRS, either the pump or Stokes beam is broadband, while the other is narrowband. By performing excitation or emission spectroscopy, signal from each vibration is detected separately. This approach allows for high chemical specificity and simultaneous multi-color imaging at a reduced imaging speed. There is a strong need for better laser sources for multiplex SRS, as most demonstrations are based on unstable electronic locking of fs- and ps-lasers.

The disclosed laser system can also be applied to other spectroscopies and label-free microscopy techniques, such as two-color, two-photon absorption (TPA) microscopy, stimulated emission (SE) microscopy, ground-state depletion (GD) microscopy and sum-frequency generation (SFG). These techniques have slightly different requirements on the laser system. Nevertheless, they share the common feature of two-color excitation with pulsed lasers.

TPA requires the sum-frequency of the two beams to be resonant with an electronic state of the sample (e.g., hemoglobin or melanin) and usually utilizes fs beams to further probe excited state dynamics. TPA is currently being explored for early detection of melanoma. SE/GD requires at least one of the two lasers to be tuned into an electronic absorption state of the sample.

All modulation transfer techniques (SRS, TPA, and SE/GD) further require a property (such as intensity, polarization or time delay) of one of the beams is modulated at a rate higher than 100 kHz allowing measurement the modulation transfer from this modulated beam to the second, originally un-modulated beam due to the nonlinear interaction in the sample.

The invention involves providing an illumination system for an imaging system such as a CRS imaging system that is economical and efficient to manufacture, and provides in particular, a CRS laser system design that is based on optical synchronization of two laser amplifiers. The approach starts with a laser oscillator with the first center frequency ω1.

This first laser is either a high-power laser (e.g., solid state Ti:Sa laser) or a low-power laser (e.g., fiber oscillator), which can be amplified to high power in consecutive steps (e.g., see reference for specific implementation). The output is split with an optical splitter. Part of the output provides the first pulse train for Coherent Raman Scattering Microscopy (i.e., either the pump or Stokes beam) or Modulation Transfer Microscopy (i.e., either the pump or probe beam). The other part of the output is fed into a frequency shifting unit, which generates optically synchronized light at a second optical frequency $\omega_2$. The frequency shifting may for example, be achieved by super-continuum generation in a high nonlinear fiber (HNLF). This new light at $\omega_2$ is then used to seed a laser amplifier at this frequency.

FIG. 4, for example, shows an illumination system that includes a laser system 14 and a combiner system 20. The laser system 14 includes a laser source 100 that provides a first train of laser pulses. The first train of laser pulses is divided, and a portion is provided to a frequency shifting system 102 and then to a picosecond amplifier system 104. A modulator 106 may be employed to modulate the train of pulses responsive to a modulation signal 36 (as discussed above), and in certain embodiments, the other signal may be modulated by a modulator 108. The combiner system 20 may include a delay unit 110 that provides an adjustable delay to ensure that the first (e.g., Stokes) and second (e.g., pump) trains of laser pulses are temporally coincident with one another. The tuning control signal 70 is coupled to the picosecond amplifier system 104 for providing tuning control of the difference frequency between the excitation trains of laser pulses.

The laser source system may be a high power oscillator, or in other embodiments as shown in FIG. 5, the laser source system 120 may include a low power oscillator 122 and an amplifier 124 for providing the first train of laser pulses.

The frequency shifting system 102 may include a highly non-linear fiber, or with reference to FIG. 6 may include a frequency shifting system 134 that includes an amplifier 136 and a highly non-linear fiber 138 (e.g., a photonic crystal fiber). The laser system 132 of the system 130 provides a first train of laser pulses 144 as discussed above that is combined with a second train of laser pulses 142 from the picosecond amplifier system 140.

The picosecond amplifier system may include a narrowband amplifier system. FIG. 7, for example shows a system 150 that includes a laser system 158 for providing a first train of pulses 164, a frequency shifting system 160, and a narrowband amplifier system 152 that includes a narrowband transmission filter 154 and an amplifier 156 for providing a second train of laser pulses 162. In other embodiments, the positions of the amplifier 156 and narrowband transmission filter 154 may be reversed.

In accordance with a further embodiment and with reference to FIG. 8, a system 190 may include a laser system 192 for providing a first train of pulses 194, a frequency shifting system 196, and a narrowband amplifier system 198 that includes a circulator 200, an amplifier 202 and a narrowband transmission filter 204. The second train of laser pulses 206 is provided from the circulator 200 as shown.

In accordance with yet a further embodiment and with reference to FIG. 9, a system 210 may include a laser system 212 for providing a first train of pulses 214, a frequency shifting system 216, and a narrowband amplifier system 218 that includes a first amplifier 220, a narrowband filter 222, and a second amplifier 224 that provides the second train of pulses 226. In accordance with a further embodiment and with reference to FIG. 10, a system 230 may include a laser system 232 for providing a first train of pulses 234, a frequency shifting system 236, and a narrowband amplifier system 238 that includes a first amplifier 240, a circulator 242, a narrowband filter 244, a second amplifier 246 and a minor 248. The second train of laser pulses 250 is provided from the circulator 242 as shown.

In accordance with a further embodiment and with reference to FIG. 11, a system 260 may include a laser system 262 for providing a first train of pulses 264, a frequency shifting system 266, and a narrowband amplifier system 268 that includes a circulator 270, first amplifier 272, a narrowband reflective filter 274, and a second amplifier 276. The second train of laser pulses 278 is provided from the circulator 270 via the second amplifier 276 as shown.

Figure 12:
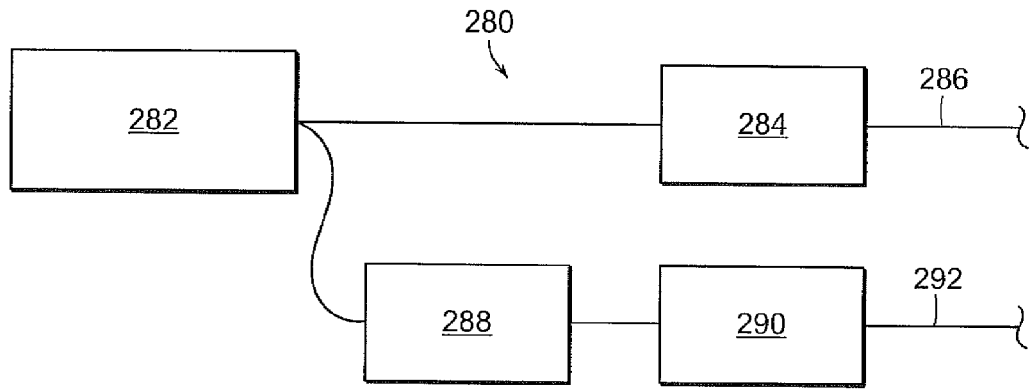
FIG. 12 shows an illustrative diagrammatic view of a portion of the illumination system of FIG. 4 employing a plurality of amplifiers in accordance with an embodiment of the invention.
Figure 13:
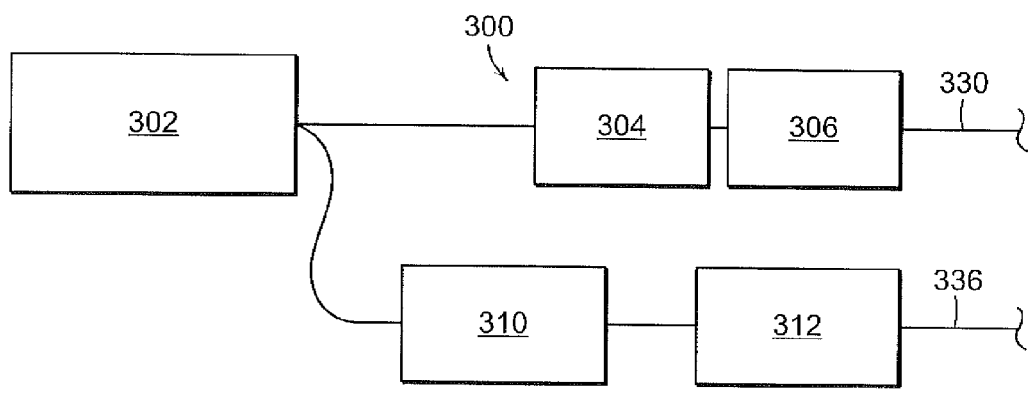
FIGS. 13-14 show illustrative diagrammatic views of a portion of the illumination system of FIG. 4 employing a plurality of amplifiers in accordance with further embodiments of the invention.
Figure 14:
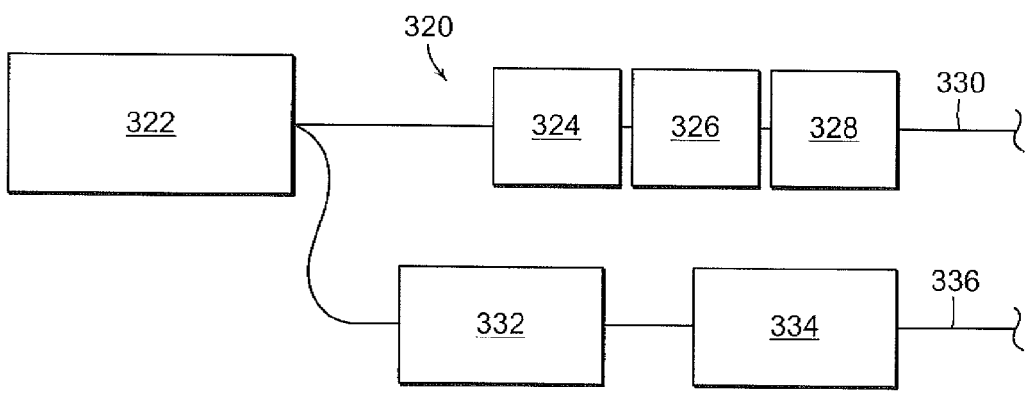

Additional embodiments for the illumination system include the following. As shown in FIG. 12, the system 280 may include a laser system 282 that provides a first train of pulses 286 via an amplifier 284, and a frequency shifting system 288 and narrowband amplifier system 290 for providing the second train of laser pulses 292. As shown in FIG. 13, the system 300 may include a laser system 302 that provides a first train of pulses 308 via a narrowband filter 304 and an amplifier 306, and a frequency shifting system 310 and narrowband amplifier system 312 for providing the second train of laser pulses 314. As shown in FIG. 14, the system 322 may include a laser system 324 that provides a first train of pulses 330 via a first amplifier 324, a narrowband filter 326 and a second amplifier 328, as well as a frequency shifting system 330 and a narrowband amplifier system 332 for providing the second train of laser pulses 334.

Additional embodiments of the invention include the following systems that employ frequency multiplication units. FIG. 15, for example shows a system 340 that includes a laser system 342 that provides a first train of pulses 344 via a frequency doubling or tripling system 346, as well as a frequency shifting system 348 and a narrowband amplifier system 350 for providing a second train of laser pulses 352. FIG. 16 shows a system 360 that includes a laser system 362 that provides a first train of pulses 364, as well as a frequency shifting system 366, a narrowband amplifier system 368, and a frequency doubling or tripling system 370 for providing a second train of laser pulses 372.

Figure 17:
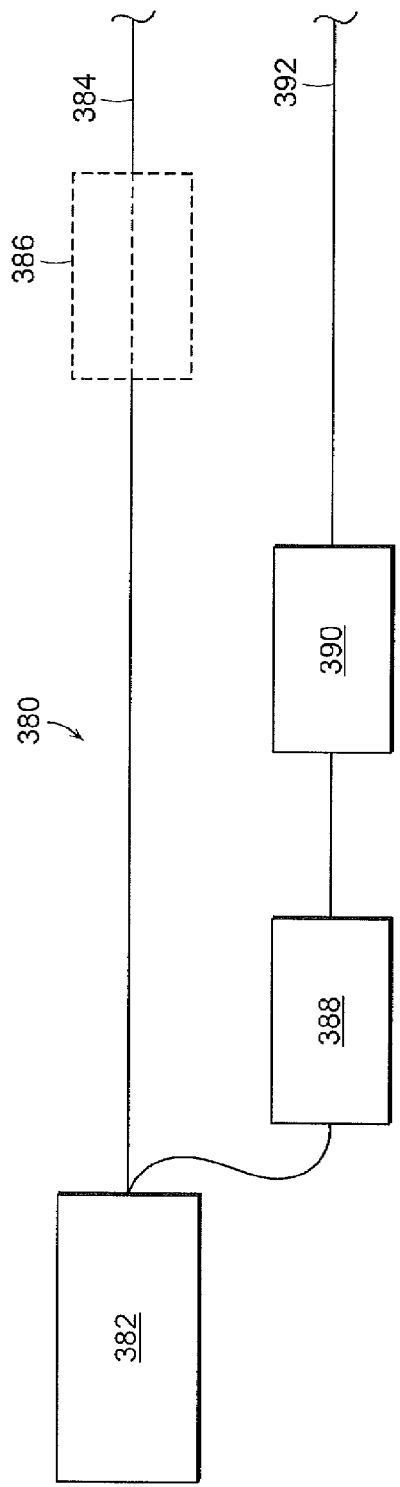
FIGS. 17-19 show illustrative diagrammatic views of an illumination system in accordance with further embodiments of the invention employing various laser systems.

In accordance with various embodiments, the gain media for systems of the invention may include a variety of doped material. For example, and as shown in FIG. 17, the system 380 may include an Erbium-doped laser system 382 for providing a first train of laser pulses 384 at 1530 nm-1610 nm (e.g., Stokes beam), as well as a frequency shifting system 388 and a Ytterbium amplifier system 390 for providing a second train of laser pulses 392 at 1010 nm-1080 nm (e.g., pump beam). In accordance with an embodiment, the system 380 may optionally further include an Erbium-doped amplifier system 386 for amplifying the first train of laser pulses as shown. The pump frequencies for the erbium-doped gain material may be about 980 nm, about 1480 nm or about 1550 nm (in-band pumping).

Figure 18:
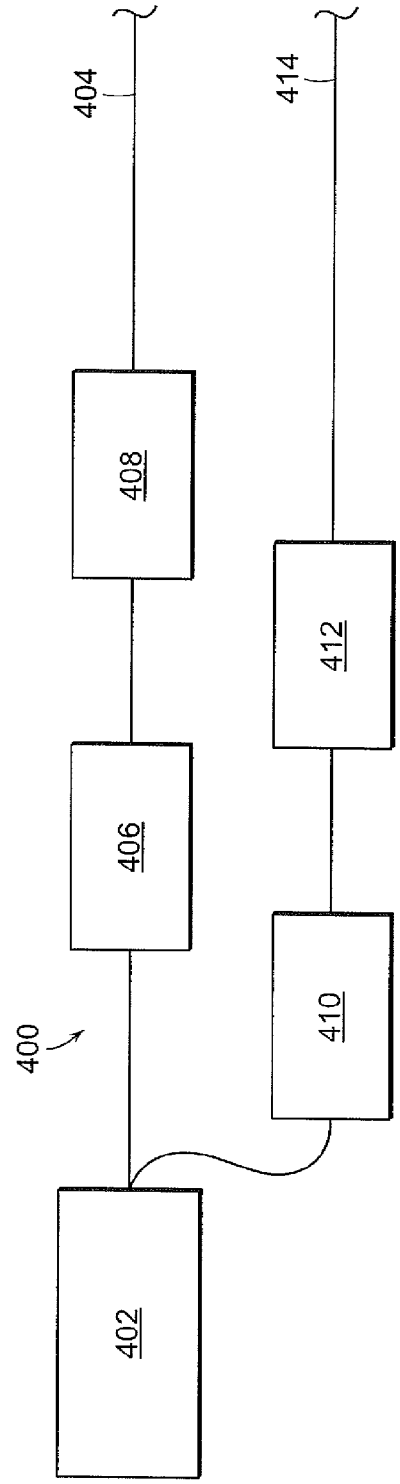

In further embodiments, the invention may provide a system 400 as shown in FIG. 18 that includes an Erbium-doped laser system (1530 nm-1610 nm), and an Erbium-doped amplifier system (1010 nm-1080 nm) and a frequency doubling system 408 for providing the first train of laser pulses (e.g., pump beam). The system 400 also includes a frequency shifting system 410 and a Ytterbium amplifier system 412 for providing the second train of laser pulses 414 at 1010 nm-1080 nm (e.g., Stokes beam).

Figure 19:
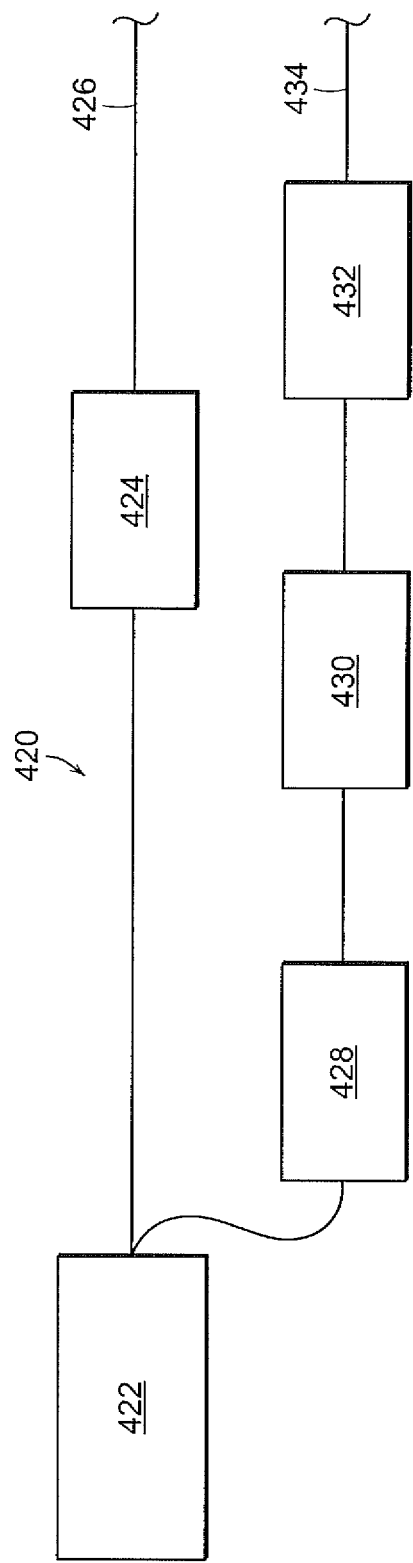

In accordance with further embodiments, the invention may provide a system 420 shown in FIG. 19 including a Ytterbium-doped laser system 422 (1010 nm-1080 nm), and a Ytterbium-doped amplifier system 424 (1010 nm-1080 nm) for providing a first train of laser pulses (e.g., a Stokes beam). The system 420 also includes a frequency shifting system 428, an Erbium-doped amplifier system 430 (1530 nm-1610 nm) and a frequency doubling unit 432 for providing a second train of laser pulses 434 (e.g., a pump beam).

With reference again to FIG. 17, in accordance with further embodiments, the laser system 382 may instead be a Ytterbium-doped laser system (1010 nm-1080 nm) and the amplifier 386 may be a Ytterbium-doped amplifier system (1010 nm-1080 nm) for providing, e.g., a Stokes beam. The amplifier system 390 may be a semiconductor amplifier system (700 nm-900 nm) that follows the frequency shifting system to provide the second train of pulses (e.g., pump beam.

In yet further embodiments, and again with reference to FIG. 17, the laser system 382 may be a titanium:sapphire (Ti:Sa) laser system (750 nm-950 nm) for directly providing a first train of laser pulses (e.g., pump beam), and the amplifier 390 may be a Ytterbium-doped amplifier system (1010 nm-1080 nm) following the frequency shifting system 388 for providing the second train of laser pulses (e.g., Stokes beam). In further embodiments, the laser system 382 may be a Thulium fiber amplifier (1800 nm-2100 nm) or a Holmium fiber amplifier (1800 nm-2100 nm), each of which may be shiftable to 900 nm-1050 nm.

In an implementation of an all fiber illumination system of the invention in which the output from an Erbium-doped fiber-oscillator is split into two arms to seed Erbium-doped and Ytterbium-doped power amplifiers. Optical synchronization is provided by frequency shifting using supercontinuum (SC) generation in a highly nonlinear fiber (HNLF). Tunable narrowband output is achieved with an in-line filter. Detailed design criteria are discussed in the research plan.

Figure 20:
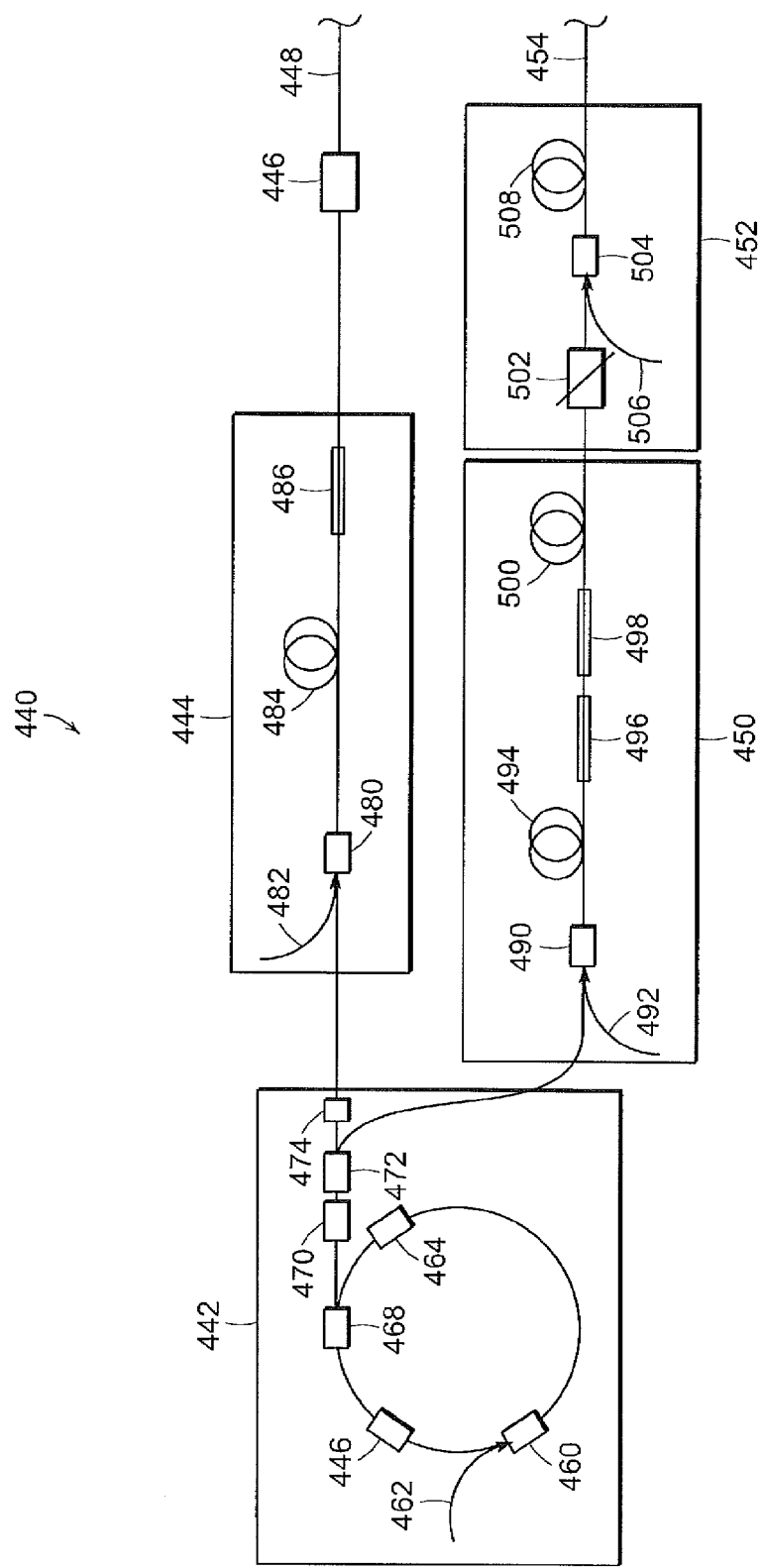
FIG. 20 shows an illustrative diagrammatic view of an illumination system in accordance with further embodiments of the invention employing a Erbium dopes fiber oscillator, as well as Erbium-doped and Ytterbium-doped power amplifiers.

In particular, the illumination system 440 of FIG. 20 includes a laser source system 442, an amplifier 444, and a frequency doubling unit 446 for providing a first train of laser pulses 448 (e.g., a pump beam). The system 440 also includes frequency shifting system 450 and an amplifier system 452 for providing a second train of pulses 454 (e.g., a Stokes beam). The laser source system 442 may be an oscillator that includes a wavelength division multiplexer 460 that receives pump illumination (980 nm) as shown at 462, an isolator 464, a carbon nanotube saturable absorber 466, an output coupler 468, another isolator 470, a 50/50 fiber splitter 472, and a modulator 474.

The first train of laser pulses from the oscillator is provided to an Erbium power amplifier 444 that includes wavelength division multiplexer that receives pump illumination (e.g., 1480 nm) as shown at 482, an Erbium-doped fiber (having normal dispersion) 484 and a compression fiber 486. The output of the Erbium power amplifier 444 is provided to a doubling crystal 446, which provides the first output train of laser pulses (pump beam) at 790 nm.

The second train of laser pulses from the oscillator is provided to the frequency shifting unit 450 that includes a wavelength division multiplexer 490 that receives pump illumination (e.g., 976 nm) as shown at 492, an Erbium-doped fiber (normal dispersion), a compression filter 496, a highly nonlinear fiber 498 and a Ytterbium-doped fiber 500. The output of the frequency shifting unit 450 is provided to a Ytterbium power amplifier 452 that includes a tunable narrowband filter 502, a wavelength division multiplexer 504 that receives pump illumination (e.g., 980 nm) as shown at 506, and a Ytterbium-doped fiber 508, which provides the second output train of laser pulses (Stokes beam) at 1010 nm-1080 nm. The first and second trains of laser pulses 448, 454 are combined as discussed above.

The Erbium fiber oscillator with a center frequency of about 1550 nm and frequency bandwidth of about 10 nm is therefore employed, and this frequency is shifted to about 1040 nm to seed the Ytterbium fiber amplifier. Amplification of the Erbium signal may be performed before or after the optical splitter. Further, the Erbium signal may also be frequency doubled or tripled to achieve shorter wavelengths as preferred for microscopy. Center frequencies can further be shifted using passive or tunable optical filters or by gain engineering (e.g., in-band pumping).

Typically, CRI systems are based on narrowband, picosecond lasers. This means, that the laser frequency bandwidth is narrower than the typical bandwidth of Raman transitions (e.g., 1 nm). In the above laser system this may either be achieved by using a laser oscillator with narrow frequency bandwidth or by using a broad-band laser system in combination with narrowband optical filters, which can be fixed frequency or tunable. The reduced intensity by frequency filtering can be restored by additional laser amplifiers.

An alternative to narrowband CRS is a technique known as spectral focusing. Instead of using narrowband pulsed, one utilizes frequency chirped broadband pulses, i.e., laser pulses with varying center frequency over time. If the chirp rate of both pulses is matched, the frequency difference is fixed and narrowband, even though the absolute frequency is swept. By tuning the time delay, different difference frequencies, i.e., different Raman peaks may be targeted. As such spectral focusing may be used to achieve fast and reproducible spectral acquisition as desired for spectroscopic differentiation with CRS. Instead of a narrowband system. Systems of the invention may also provide pulses for spectral focusing CRS by using broadband amplifiers and adjusting the chirp rate with a dispersion unit (e.g., optical fibers with well-known dispersion). The delay may be scanned automatically or manually with an optical delay stage.

Laser systems of various embodiments of the invention may also provide excitation pulses for multiplex CRS. In multiplex CRS, either pump or Stokes beam is broadband and narrowband, respectively. This means that multiple Raman transitions are excited simultaneously. By performing either excitation or emission spectroscopy, it is possible to detect the signal from each vibrations separately and simultaneously, i.e., in a multiplexed fashion. This means that multicolor images at multiple vibrations may be acquired. In another implementation of the disclosed laser system multiplex CRS can be achieved by implementing a broadband first train of pulses and a narrowband second train of pulses or vice versa.

As discussed above with reference to FIG. 4, either of the first and second trains of laser pulses may pass through an optical delay device to ensure coincident timing when the trains of laser pulses are combined, and either the first train of laser pulses or the second train of laser pulses may be modulated prior to combining the two trains of laser pulses.

Figure 21A:
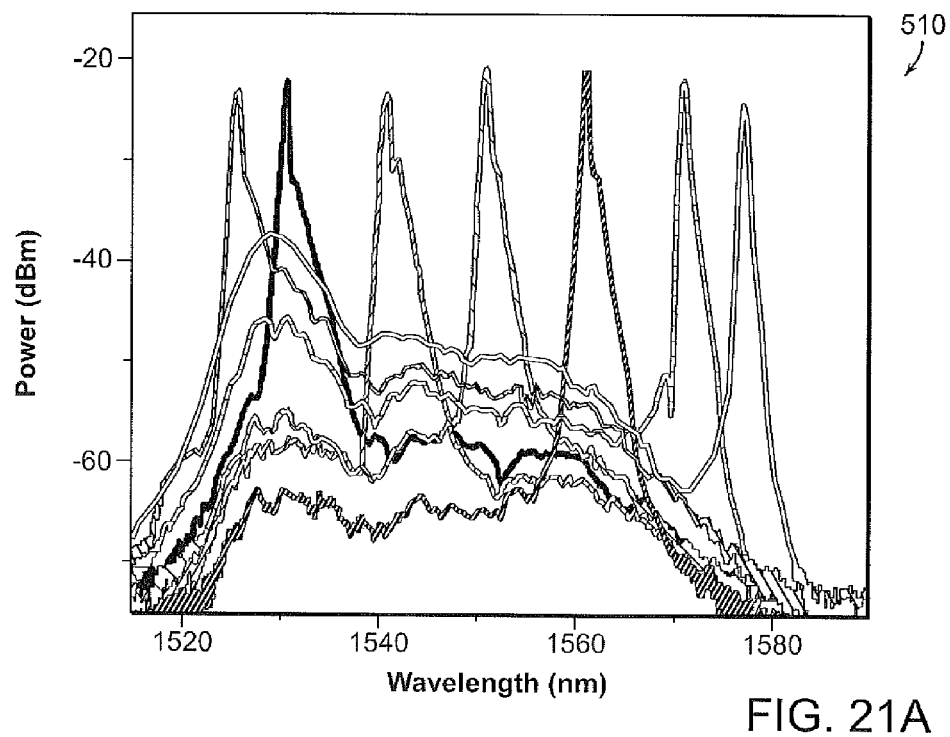
FIGS. 21A-21B show illustrative graphical representations of tuning ranges for illumination sources in accordance with embodiments of the present invention employing different gain mediums.
Figure 21B:
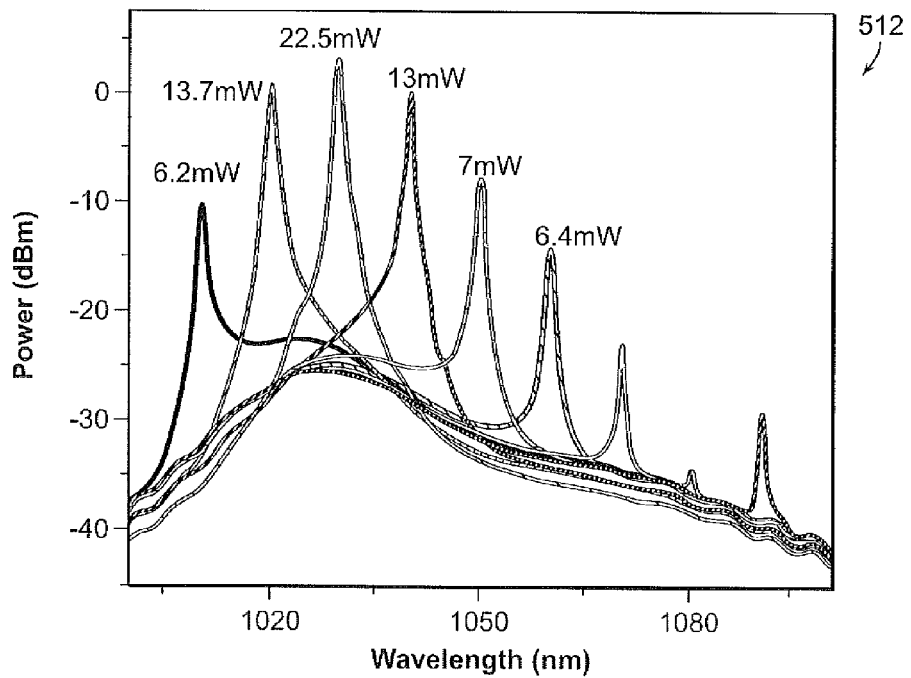

FIG. 21A shows at 510 the narrow bandwidth of the output spectra and the tuning range for the Erbium-doped amplifier, and FIG. 21B shows at 512 the narrow bandwidth and tuning range for the Ytterbium-doped amplifier.

In accordance with further embodiments, the picosecond amplifier may include a chirped amplifier system, and the illumination system may be used in a spectral focusing imaging system, which requires lasers with a bandwidth smaller or comparable to the typical Raman linewidth. If broadband lasers are chirped linearly however, (i.e., the instantaneous laser frequency changes over time), and that the same rate for both pump and Stokes, the difference frequency is essentially narrowband. Rather than tuning the difference by changing the center frequency of the lasers, CRI spectra may be acquired by tuning the time delay.

Figure 22:
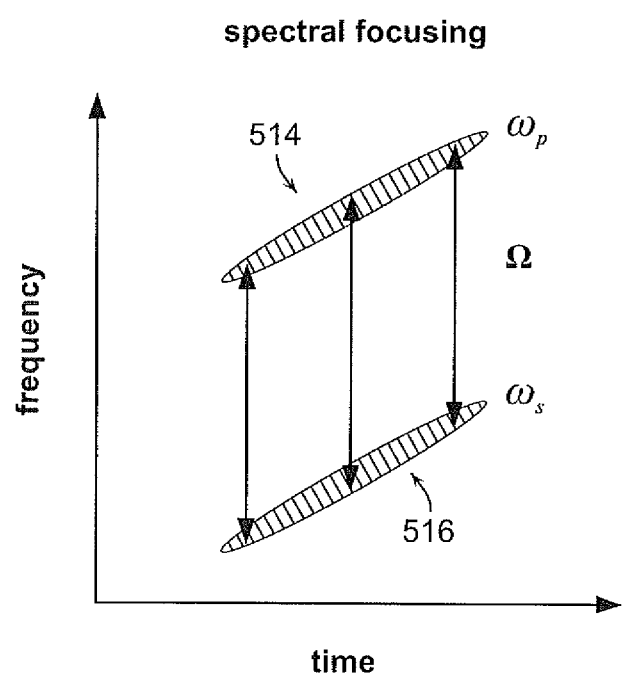
FIG. 22 shows an illustrative graphical representation of the relationship between frequency and time, showing changes in the pulses over time and frequency that permits spectral focusing of the excitation illumination in accordance with an embodiment of the invention.

FIG. 22 shows that the frequency of each of the pump and Stokes fields may be varied over time and frequency, yet provide the same difference frequency as shown at 514 and 516 in FIG. 22. This provides for spectral focusing. Specifically, it shows that an amplified frequency-shifted train of pulses may be provided having pulses with a temporally evolving instantaneous frequency over the picosecond pulse duration.

Figure 23:
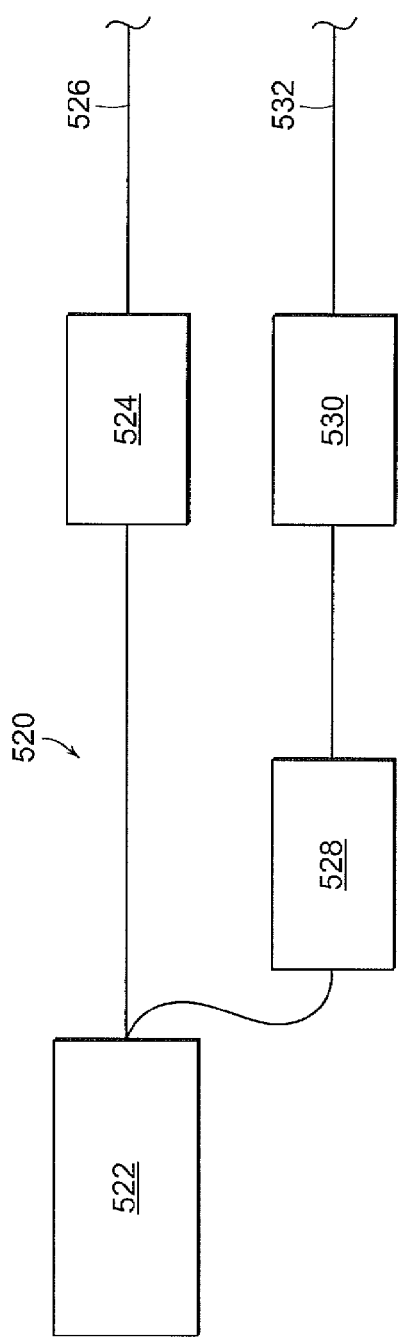
FIG. 23 shows an illustrative diagrammatic view of a portion of the illumination system of FIG. 4 employing a chirped amplifier system in accordance with an embodiment of the invention.

FIG. 23, for example, shows a system in accordance with a further embodiment of the present invention that includes a laser system (as discussed above) that provides a first train of laser pulses to a chirped control system 524, which provide the first output train of laser pulses 526. The system 520 also includes a frequency shifting system 528 (as discussed above) and a chirped amplifier system 530 that provides the second output train of laser pulses 532. The laser system 522, the gain media, and the frequency shifting system 528, may be as described above with reference to FIGS. 1-20.

Figure 24:
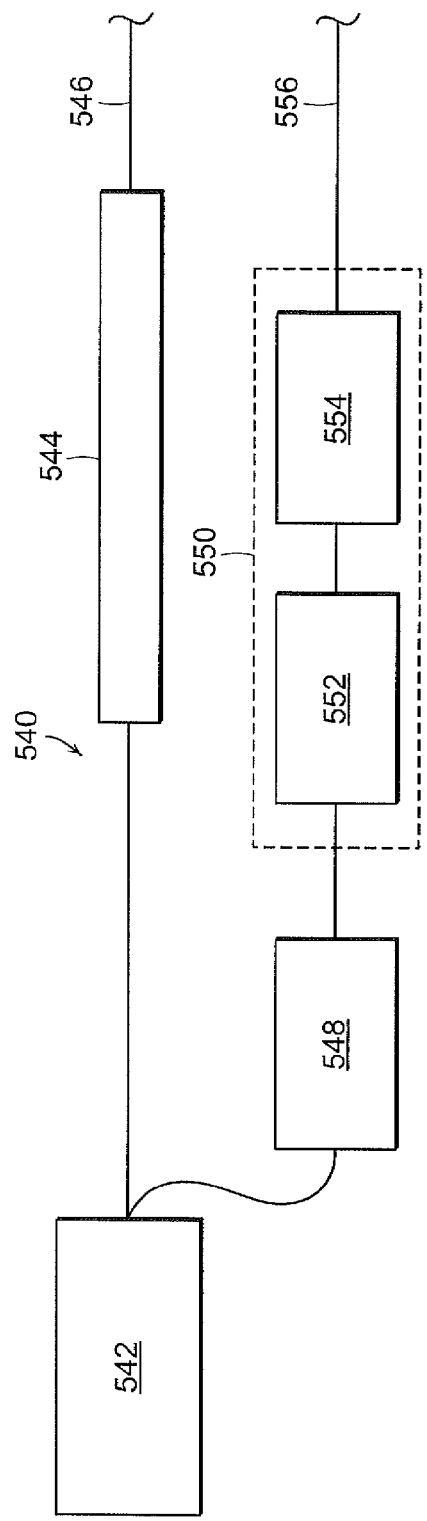
FIG. 24 shows an illustrative diagrammatic view of a portion of the illumination system of FIG. 4 employing a chirped amplifier system in accordance with another embodiment of the invention.

As shown in FIG. 24, a system 540 in accordance with a further embodiment may include a laser system 542 and a chirped control system 544 for providing the first train of laser pulses 546. The system 540 may also include a frequency shifting system 548, as well as a chirped amplifier system 550 that includes a chirp unit 552 (e.g., a fiber or prism pain) and an amplifier 554, which provides the second output train of laser pulses 556. Again, the laser system 542, the gain media, and the frequency shifting system 548, may be as described above with reference to FIGS. 1-20.

Figure 25:
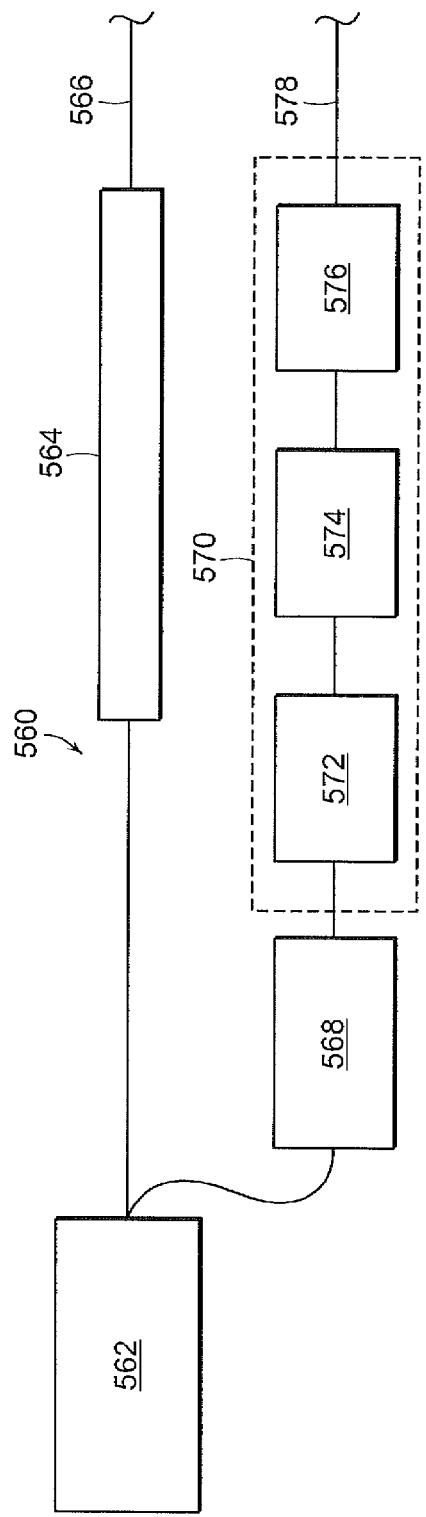
FIGS. 25-30 show illustrative diagrammatic views of a portion of the illumination system of FIG. 4 employing a chirped amplifier system in accordance with further embodiments of the invention.

FIG. 25 shows a system 560 in accordance with a further embodiment that includes a laser system 562 and a chirped control system 564 for providing the first train of laser pulses 566. The system 560 also includes a frequency shifting system 568, as well as a chirped amplifier system 570 that includes a broadband amplifier 572, chirp unit 572 (e.g., a fiber or prism pain) and an amplifier 574, which provides the second output train of laser pulses 576. Again, the laser system 562, the gain media, and the frequency shifting system 568, may be as described above with reference to FIGS. 1-20.

Figure 26:
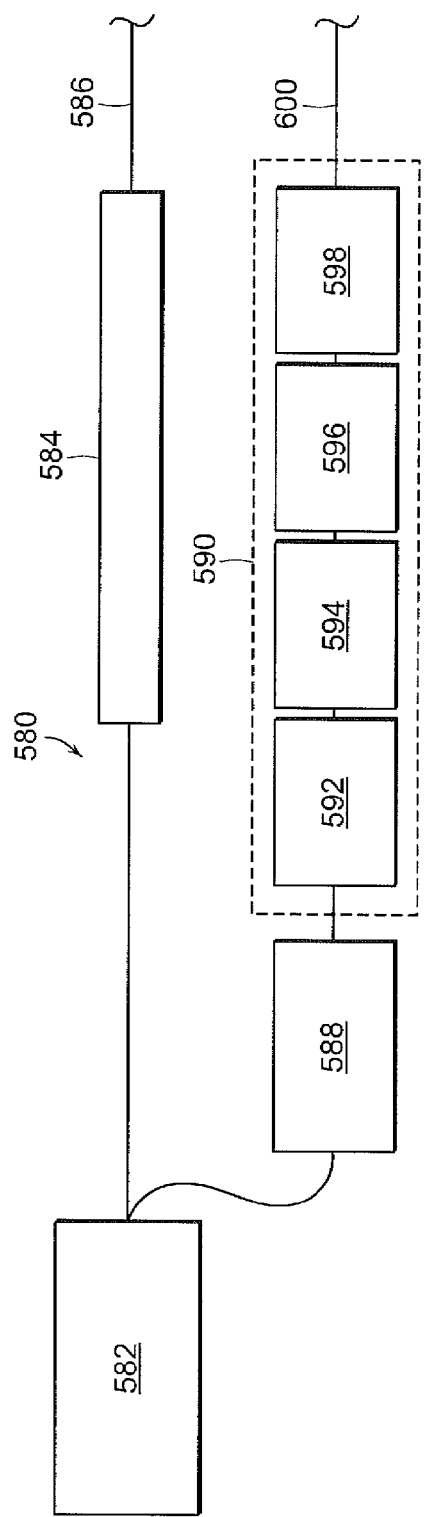

FIG. 26 shows a system 580 in accordance with a further embodiment that includes a laser system 582 and a chirped control system 584 for providing the first train of laser pulses 586. The system 580 also includes a frequency shifting system 588, as well as a chirped amplifier system 590 that includes a broadband amplifier 592, an amplifier 594, frequency doubling or tripling unit 596, and a chirp unit 598 (e.g., a fiber or prism pain), which provides the second output train of laser pulses 600. Again, the laser system 582, the gain media, and the frequency shifting system 588, may be as described above with reference to FIGS. 1-20, and the frequency doubling or tripling unit 596 may be as discussed above with reference to FIGS. 15 and 16.

Figure 27:
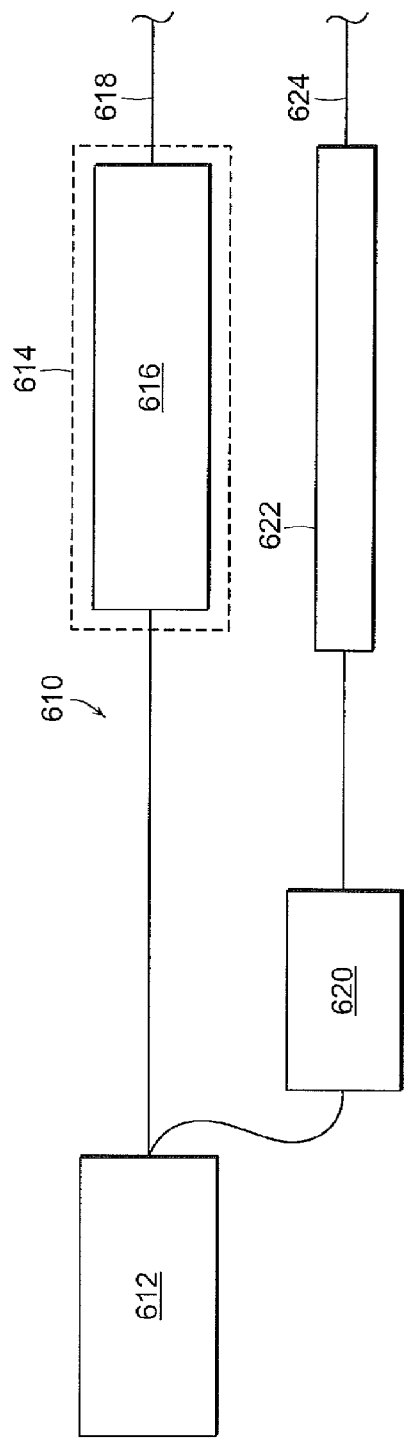

FIG. 27 shows a system 610 in accordance with a further embodiment that includes a laser system 612 and a chirped control system 614 that includes a chirp unit 616 (e.g., fiber or prism pain) for providing the first train of laser pulses 618. The system 610 also includes a frequency shifting system 620, as well as a chirped amplifier system 622, which provides the second output train of laser pulses 624. Again, the laser system, the gain media, 612 and the frequency shifting system 620, may be as described above with reference to FIGS. 1-20.

Figure 28:
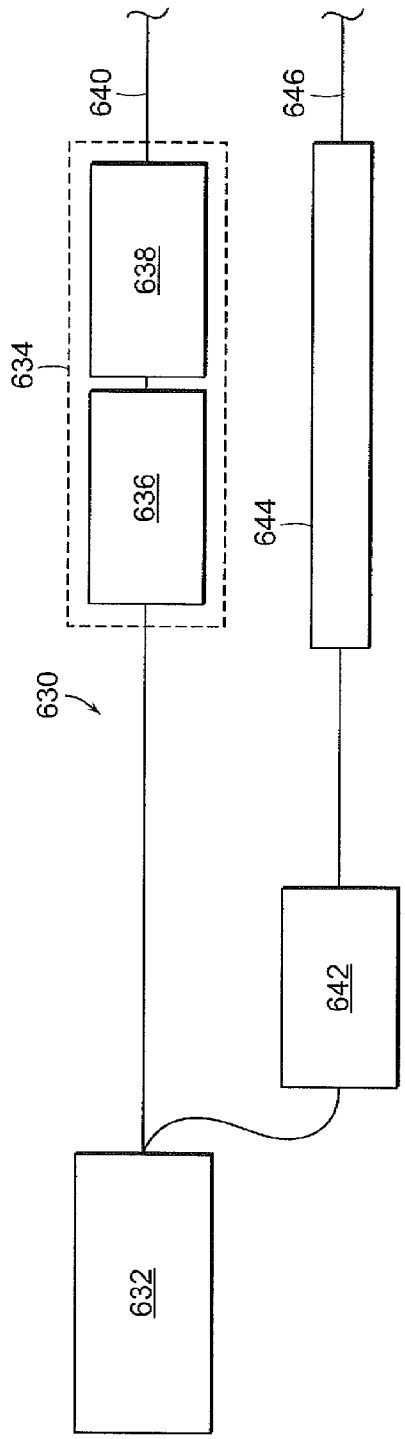

FIG. 28 shows a system 630 in accordance with a further embodiment that includes a laser system 632 and a chirped control system 634 that includes a chirp unit 616 (e.g., fiber or prism pain) and an amplifier 638 for providing the first train of laser pulses 640. The system 630 also includes a frequency shifting system 642, as well as a chirped amplifier system 644, which provides the second output train of laser pulses 646. Again, the laser system 632, the gain media, and the frequency shifting system 642, may be as described above with reference to FIGS. 1-20.

Figure 29:
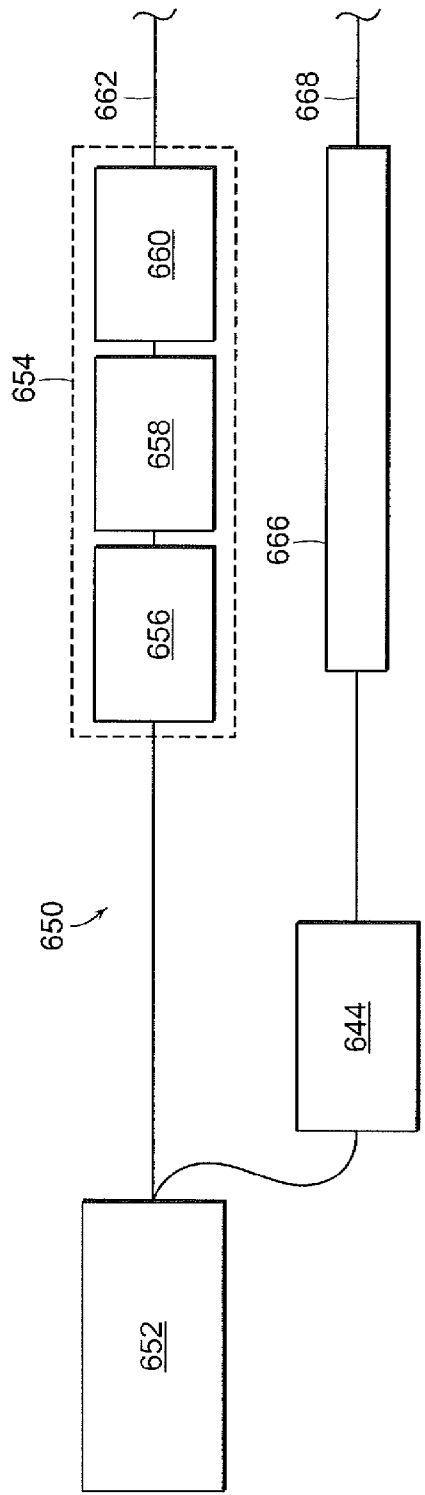

FIG. 29 shows a system 650 in accordance with a further embodiment that includes a laser system 652 and a chirped control system 654 that includes a broadband filter 656, a chirp unit 658 (e.g., fiber or prism pain) and an amplifier 660 for providing the first train of laser pulses 662. The system 650 also includes a frequency shifting system 664, as well as a chirped amplifier system 666, which provides the second output train of laser pulses 668. Again, the laser system 652 and the frequency shifting system 664, the gain media, may be as described above with reference to FIGS. 1-20.

Figure 30:
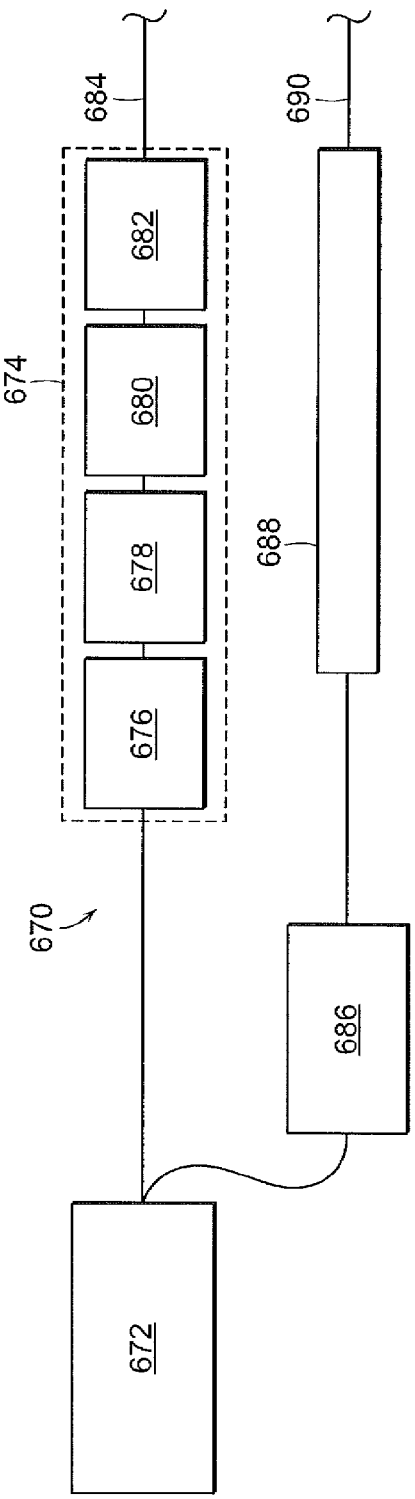

FIG. 30 shows a system 670 in accordance with a further embodiment that includes a laser system 672 and a chirped control system 674 that includes a broadband filter 676, an amplifier 678, a frequency doubling or tripling unit 680, and a chirp unit 682 (e.g., fiber or prism pain) for providing the first train of laser pulses 684. The system 670 also includes a frequency shifting system 686, as well as a chirped amplifier system 688, which provides the second output train of laser pulses 690. Again, the laser system 672, the gain media, and the frequency shifting system 686, may be as described above with reference to FIGS. 1-20.

Figure 31:
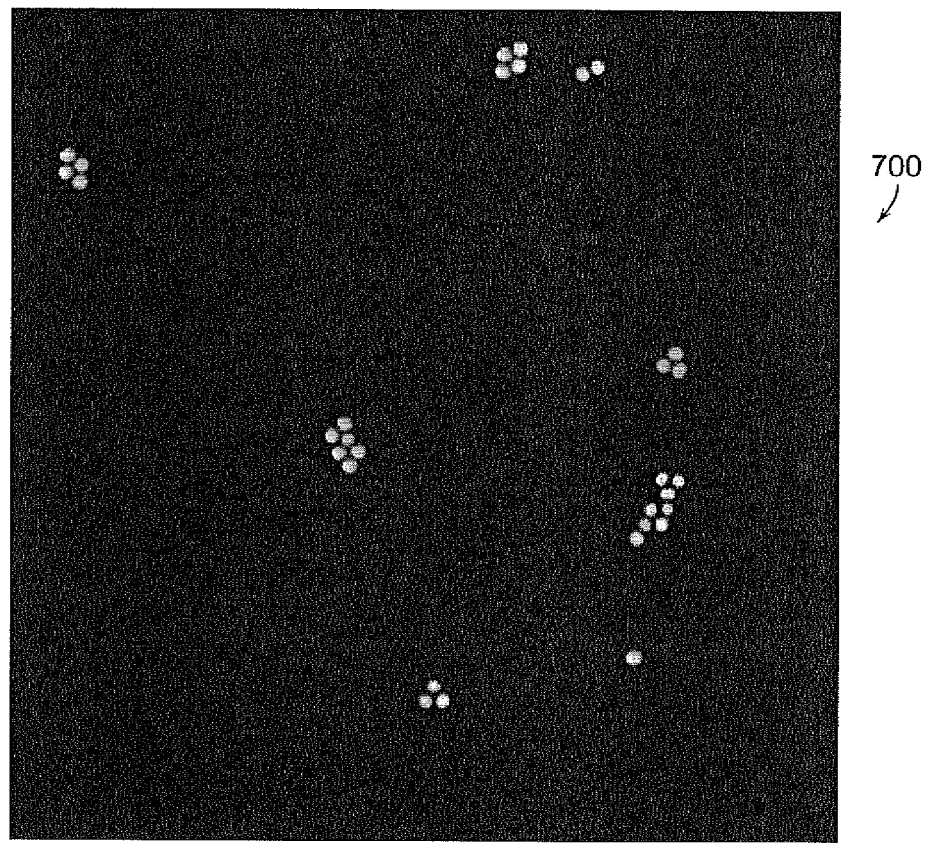
FIG. 31 shows an illustrative photographic representation of a CRS image of polystyrene beads obtained using an illumination system of the present invention.
Figure 32:
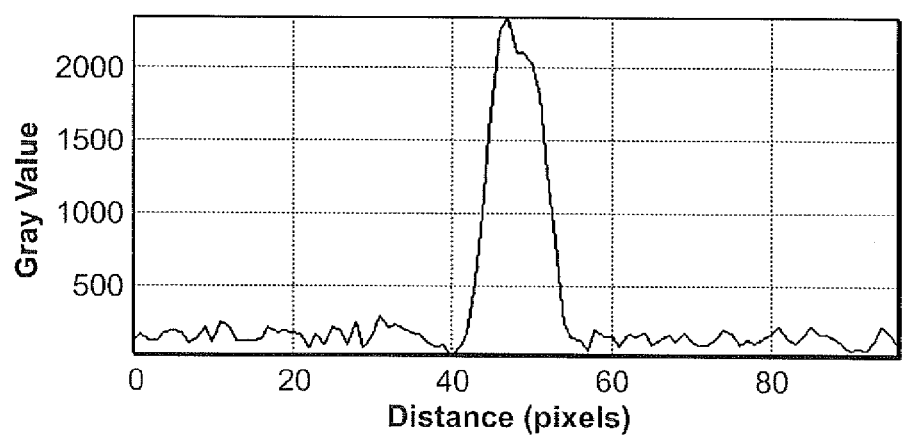
FIG. 32 shows an illustrative graphical representation of gray value intensities along a cross-section of the photographic representation of FIG. 31.

FIG. 31 shows at 700 an image taken using a CRS system with an illumination system in accordance with an embodiment of the present invention wherein the size is 1 μm, the sampling was 512 by 512 pixels, and the imaging speed was one frame per second (4 μs/pixel). FIG. 32 shows at 710 a cross-section of the image 700 with a signal to noise ratio of greater than 25.

FIG. 33A shows at 720 an image taken using a CRS system with an illumination system in accordance with an embodiment of the present invention of CH2 vibrations (lipids) using a Stokes beam of 1018 nm, a pump beam of 789 nm and a wavenumber of 2850 $CM^{-1}$. FIG. 33B shows at 722 an image taken using a CRS system with an illumination system in accordance with an embodiment of the present invention of CH3 vibrations (proteins) using a Stokes beam of 1028 nm, a pump beam of 789 nm and a wavenumber of 2950 $CM^{-1}$. FIG. 34 shows at 730 a combination of the images 720, 722 of FIGS. 33A and 33B.

Those skilled in the art will appreciate that numerous modifications and variations may be made to the above disclosed embodiments without departing from the spirit and scope of the claims.

What is claimed is:

1. An illumination system for providing dual-excitation wavelength illumination for non-linear optical microscopy and micro-spectroscopy, said illumination system comprising:
   a laser system including a laser oscillator for providing a first train of pulses at a center optical frequency $\omega_1$;
   an optical splitting means for dividing the first train of pulses at the center optical frequency $\omega_1$ into a first split train of pulses and a second split train of pulses;
   a frequency shifting system for shifting the optical frequency of the first split train of pulses to provide a frequency shifted train of pulses; and
   a picosecond amplifier system for amplifying the frequency shifted train of pulses to provide an amplified frequency-shifted train of pulses having a pulse duration of at least 0.5 picoseconds.

2. The illumination system as claimed in claim 1, wherein said picosecond amplifier is a narrowband amplifier.

3. The illumination system as claimed in claim 2, wherein said narrowband amplifier is tunable to provide that the difference frequency of the amplified frequency-shifted train of pulses and the second split train of pulses may be varied.

4. The illumination system as claimed in claim 2, wherein said narrowband amplifier system includes a narrowband filter.

5. The illumination system as claimed in claim 2, wherein said narrowband amplifier system includes a plurality of amplifiers in series.

6. The illumination system as claimed in claim 1, wherein said laser system includes a high power oscillator.

7. The illumination system as claimed in claim 1, wherein said laser system includes a low power oscillator and an amplifier.

8. The illumination system as claimed in claim 1, wherein said illumination system further includes a laser amplifier for amplifying the second split train of pulses.

9. The illumination system as claimed in claim 1, wherein said frequency shifting system includes a highly non-linear fiber.

10. The illumination system as claimed in claim 1, wherein said frequency shifting system includes a photonic crystal fiber.

11. The illumination system as claimed in claim 1, wherein said frequency shifting system further includes a laser amplifier.

12. The illumination system as claimed in claim 1, wherein said picosecond amplifier is a chirp amplifier to provide an amplified frequency-shifted train of pulses having pulses with a temporally evolving instantaneous frequency over the picosecond pulse duration.

13. The illumination system as claimed in claim 12, wherein said chirped amplifier system includes a chirp unit and an amplifier.

14. The illumination system as claimed in claim 13, wherein said chirped amplifier system further includes a broadband filter.

15. The illumination system as claimed in claim 14, wherein system further includes a chirp control system in the second split train of pulses.

16. The illumination system as claimed in claim 1, wherein system further includes:
   a combiner for combining the amplified frequency-shifted train of pulses and the second split train of pulses from the optical splitting means; and
   adjusting means for adjusting a time delay between the amplified frequency-shifted train of pulses and the second split train of pulses with sub-picosecond precision to provide a collinear output of the dual-excitation wavelength illumination for the non-linear optical microscopy or micro-spectroscopy system.

17. The illumination system as claimed in claim 1, wherein said laser system is one of a Ytterbium fiber laser and an Erbium fiber laser.

18. The illumination system as claimed in claim 1, wherein said laser system is a Titanium Sapphire laser.

19. The illumination system as claimed in claim 1, wherein said picosecond amplifier system is one of an Erbium fiber amplifier, a Ytterbium fiber amplifier, a Thulium fiber amplifier, and a Holmium fiber amplifier.

20. The illumination system as claimed in claim 1, wherein the output of the picosecond amplifier system is frequency doubled (SHG) or tripled (THG).

21. The illumination system as claimed in claim 1, wherein the second split train of pulses from the optical splitting means is frequency doubled (SHG) or tripled (THG).

* * * * *